US011690616B2

(12) United States Patent
Fein et al.

(10) Patent No.: US 11,690,616 B2
(45) Date of Patent: Jul. 4, 2023

(54) ORTHOPEDIC STAPLE INSERTION

(71) Applicant: Arthrex, Inc., Naples, FL (US)

(72) Inventors: Paul Fein, Maynard, MA (US); Alexander DelMonaco, Chelmsford, MA (US); Chris Powell, Naples, FL (US)

(73) Assignee: Arthrex, Inc., Naples, FL (US)

( * ) Notice: Subject to any disclaimer, the term of this patent is extended or adjusted under 35 U.S.C. 154(b) by 83 days.

(21) Appl. No.: 17/502,495

(22) Filed: Oct. 15, 2021

(65) Prior Publication Data

US 2022/0117599 A1 Apr. 21, 2022

Related U.S. Application Data

(60) Provisional application No. 63/226,451, filed on Jul. 28, 2021, provisional application No. 63/092,720, filed on Oct. 16, 2020.

(51) Int. Cl.
*A61B 17/068* (2006.01)
*A61B 17/072* (2006.01)
*A61B 17/064* (2006.01)

(52) U.S. Cl.
CPC ...... *A61B 17/0682* (2013.01); *A61B 17/0642* (2013.01); *A61B 17/0644* (2013.01); *A61B 17/072* (2013.01); *A61B 2017/07228* (2013.01)

(58) Field of Classification Search
CPC .............. A61B 17/0682; A61B 17/072; A61B 17/0644; A61B 17/0642
See application file for complete search history.

(56) References Cited

U.S. PATENT DOCUMENTS

| | | |
|---|---|---|
| 4,493,317 A | 1/1985 | Klaue |
| 5,044,540 A | 9/1991 | Dulebohn |
| 5,497,933 A | 3/1996 | DeFonzo et al. |
| 5,697,933 A | 12/1997 | Gundlapalli et al. |
| 6,083,225 A | 7/2000 | Winslow et al. |
| 6,960,216 B2 | 11/2005 | Kolb et al. |
| 7,530,484 B1 | 5/2009 | Durrani |
| 8,393,517 B2 | 3/2013 | Milo |
| 8,584,853 B2 | 11/2013 | Knight et al. |
| 9,017,331 B2 | 4/2015 | Fox |
| 9,095,338 B2 | 8/2015 | Taylor et al. |
| 9,101,349 B2 | 8/2015 | Knight et al. |
| 9,204,932 B2 | 12/2015 | Knight et al. |
| 9,339,268 B2 | 5/2016 | Fox |
| 9,451,957 B2 | 9/2016 | Fox |
| 9,486,212 B2 | 11/2016 | Miller et al. |
| 9,743,926 B2 | 8/2017 | Fox |
| 9,907,551 B2 | 3/2018 | Seavey et al. |
| 9,931,115 B2 | 4/2018 | Morgan et al. |
| 10,010,320 B2 | 7/2018 | Wahl |
| 10,052,103 B2 | 8/2018 | Wahl |
| 10,105,134 B2 | 10/2018 | Biedermann et al. |
| 10,182,808 B2 | 1/2019 | Spivey et al. |
| 10,188,388 B2 | 1/2019 | Handie |
| 10,456,131 B2 | 10/2019 | Cheney et al. |

(Continued)

*Primary Examiner* — Nathaniel C Chukwurah
(74) *Attorney, Agent, or Firm* — Carlson, Gaskey & Olds, P.C.

(57) ABSTRACT

A multi-staple inserter and drill guide, and methods of use thereof, are disclosed therein. The orthopedic staples can also be used in addition to interfragmentary screws to apply further compression of the bone fragments.

20 Claims, 21 Drawing Sheets

(56) References Cited

U.S. PATENT DOCUMENTS

| | | |
|---|---|---|
| 10,507,021 B2 | 12/2019 | Miller et al. |
| 10,512,459 B2 | 12/2019 | Fox |
| 10,588,628 B2 | 3/2020 | Vasta |
| 10,610,221 B2 | 4/2020 | Wahl |
| 10,610,222 B2 | 4/2020 | Wahl |
| 10,779,816 B2 | 9/2020 | Goldstein et al. |
| 2004/0204710 A1 | 10/2004 | Patel et al. |
| 2005/0096660 A1 | 5/2005 | Allen |
| 2007/0093848 A1 | 4/2007 | Harris et al. |
| 2007/0233150 A1 | 10/2007 | Blain et al. |
| 2009/0018556 A1 | 1/2009 | Prandi |
| 2009/0024131 A1 | 1/2009 | Metzger et al. |
| 2012/0150186 A1 | 6/2012 | Hajianpour |
| 2013/0206815 A1 | 8/2013 | Fox |
| 2013/0211462 A1 | 8/2013 | Walker |
| 2013/0213843 A1 | 8/2013 | Knight et al. |
| 2014/0097228 A1 | 4/2014 | Taylor et al. |
| 2014/0358187 A1 | 12/2014 | Taber et al. |
| 2015/0282819 A1 | 10/2015 | Austin et al. |
| 2016/0199060 A1 * | 7/2016 | Morgan .................. A61B 17/10 227/175.1 |
| 2016/0235460 A1 * | 8/2016 | Wahl .................... A61B 17/068 |
| 2017/0000482 A1 | 1/2017 | Averous et al. |
| 2017/0043415 A1 | 2/2017 | Cheney et al. |
| 2017/0231625 A1 | 8/2017 | Handie |
| 2017/0252036 A1 | 9/2017 | Palmer et al. |
| 2017/0319219 A1 | 11/2017 | Serbousek et al. |
| 2017/0348112 A1 | 12/2017 | Goldberg |
| 2018/0271521 A1 | 9/2018 | Wahl |
| 2019/0069910 A1 | 3/2019 | Powell et al. |
| 2019/0150921 A1 | 5/2019 | Fonte et al. |
| 2020/0046381 A1 | 2/2020 | Kehres et al. |

\* cited by examiner

ORTHOPEDIC STAPLE INSERTION

REFERENCE TO RELATED APPLICATIONS

This disclosure claims the benefit of U.S. Provisional Application No. 63/092,720 filed Oct. 16, 2020 and U.S. Provisional Application No. 63/226,451, filed on Jul. 28, 2021, the entire disclosures of which are hereby incorporated by reference.

BACKGROUND

An inserter installs a staple across a fracture line of a fractured bone to maintain a compressive load across a fracture line during healing. A drill guide provides the correct alignment between a drill and a bone to form a hole in the bone to create a screw passage to receive an interfragmentary screw. Interfragmentary screws and staples can be used together to maintain a compressive load across a fracture line.

SUMMARY

Described herein are methods and materials for implanting staples comprising shape memory material (e.g., nitinol, PEEK, etc.). In particulars, the methods and materials described herein include implanting more than one staple using a single inserter. The drill guides described herein provide a surgeon the ability to predetermine the holes for the staple(s) that can be inserted simultaneously or sequentially. In an embodiment, an interfragmentary screw is also used to compress the fracture in addition to staples, and the screw's trajectory does not interfere with the staples.

An insertion system includes a multi-staple inserter that is used to implant at least two staples. In an embodiment, a multi-staple inserter constrains and holds a plurality of staples in a strained state for implantation across a fracture line in a fractured bone. The multi-staple inserter includes a body having an internal threaded region and a threaded rod configured to mate with the internal threaded region. A pair of plates are mounted to each side of the body of the multi-staple inserter, and a staple is releasably mounted to each of the pair of plates. A handle is turned in a first direction to translate the threaded rod distally to transfer force to bridges of the staples so that the staples move from an unrestrained state to a strained state. Elastic hinge regions of the staples bend about pins of the plates to pivot legs of the staples outwardly. The multi-staple inserter can hold the staples in the strained state for implantation. Upon insertion of the strained staples into the fracture site, the multi-staple inserter removes constraint from the staples.

An interfragmentary drill guide as disclosed herein is used to drill holes in a bone for the placement of at least one staple and an interfragmentary screw. The interfragmentary drill guide includes a body including at least one hole that receives a drill to form a screw passage in a fractured bone. The hole is shaped to guide the drill so the screw passage will have a specific trajectory within a fractured bone that does not interfere with the staple(s). In an embodiment, the interfragmentary drill guide includes two slots that each receive a portion of a drill guide used to drill holes for the staple. The interfragmentary drill guide can also include features that align the interfragmentary drill guide relative to bone either before or after installation of a staple. The interfragmentary drill guide can include an elongated handle.

A method of inserting more than one staple into a bone includes moving a handle of a multi-staple inserter of an insertion system in a first direction to configure at least two staples mounted to a body of the multi-staple inserter from an unrestrained state to a strained state to bend a bridge of the staples to move a pair of legs of the staples to be substantially perpendicular to the bridge, inserting each of the pair of legs of the staples into a set of holes in the bone, and releasing the staples from the body of the multi-staple inserter. Additionally, each of the pair of legs of the staples can be attached to the bridge at a pair of first elastic hinge regions, and each of the pair of elastic hinge regions of the staple can be mounted on a pair of distal pins that are each mounted to a pair of plates. The pair of plates are each mounted to a side of the body of the multi-staple inserter by a proximal pin. Methods also include at least two staples moving from the strained state to the unrestrained state, either simultaneously or sequentially.

A method also includes compressing a fracture. Methods of compressing a fracture include aligning a body of an interfragmentary drill guide relative to a bone such that drill slots for staple placement are on either side of a fracture line and a guide for a drill passage is on opposing sides of the fracture line to receive an interfragmentary screw that does not interfere with the staples. In particular, methods include positioning a drill guide in each of the two slots of the interfragmentary drill guide to form a drill passage each located on opposing sides of the facture line of the bone that each receive a leg of a staple and forming a screw passage through at least one hole of the body of the interfragmentary drill guide. The screw passage has a trajectory that crosses the fracture line of the bone that does not intersect the legs of the staple.

These and other embodiments are described in more detail below.

DETAILED DESCRIPTION

Figure 1:
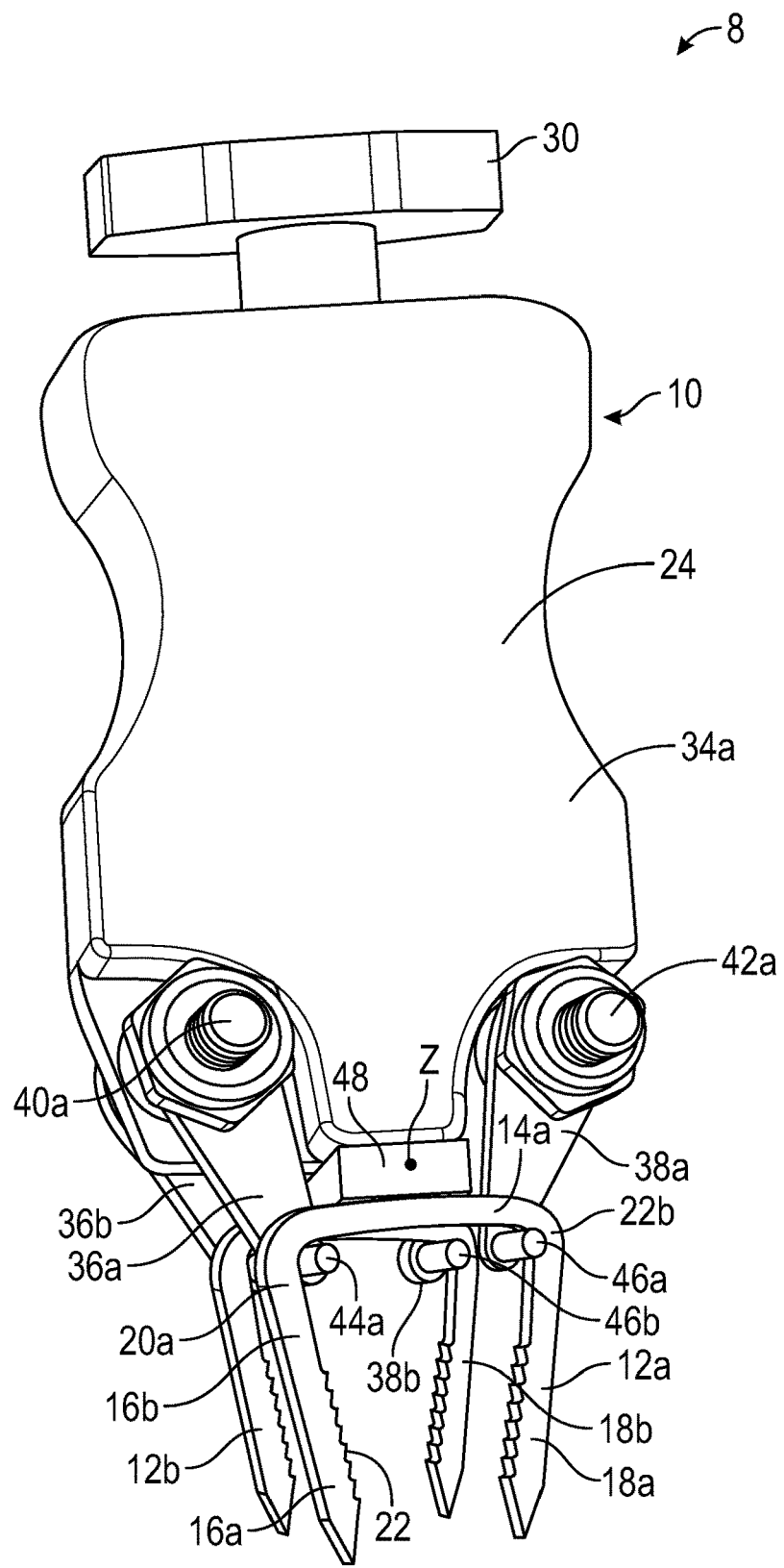
FIG. 1 illustrates a perspective view of an insertion system including a multi-staple inserter and two staples.

An insertion system includes a multi-staple inserter that constrains and holds a plurality of staples in a strained state for implantation across a fracture line in a fractured bone. The multi-staple inserter includes a body having an internal threaded region and a threaded rod configured to mate with the internal threaded region. A pair of plates are mounted to each side of the body of the multi-staple inserter, and a staple is releasably mounted to each of the pair of plates. A handle is turned in a first direction to translate the threaded rod distally to transfer force to bridges of the staples so that the staples move from an unrestrained state to a strained state. Elastic hinge regions of the staples bend about pins of the plates to pivot legs of the staples outwardly. The multi-staple inserter can hold the staples in the strained state for implantation. Upon insertion of the strained staples into the fracture site, the multi-staple inserter removes constraint from the staples.

An interfragmentary drill guide is used to drill a screw passage that spans a fracture line in a fractured bone. The screw passage receives an interfragmentary screw to supplement a staple that is used to repair a fracture. The interfragmentary drill guide includes a body including at least one hole that receives a drill to form a screw passage in a fractured bone. The hole is shaped to guide the drill so the screw passage will have a specific trajectory within a fractured bone. The interfragmentary drill guide also includes two slots that each receive a portion of a drill guide used to drill holes for the staple. The interfragmentary drill guide can also include features that align the interfragmentary drill guide relative to bone either before or after installation of a staple. The interfragmentary drill guide can include an elongated handle.

In one example, an insertion system includes a body including a first side and an opposing second side. A first staple includes a first bridge and a first pair of legs each attached to the first bridge at a first elastic hinge region, and a second staple includes a second bridge and a second pair of legs are each attached to the second bridge at a second elastic hinge region. The staples are mounted to the body, and the staples are identical and comprise Nitinol. The insertion system includes a first pair of plates each mounted to the first side of the body by a first proximal pin and a second pair of plates each mounted to the second side of the body by a second proximal pin. Each of the first pair of plates includes a first distal pin, and each of the second pair of plates includes a second distal pin. The first staple is mounted on the first distal pins, and the second staple is mounted on the second distal pins. Each of the first distal pins of the first pair of plates are located under one of the first elastic hinge regions of the first staple, and each of the second distal pins of the second pair of plates are located under one of the second elastic hinge regions of the second staple. The insertion system includes a handle moveable in a first direction and an opposing second direction and a plunger having a proximal end and a distal end. Movement of the handle causes the distal end of the plunger to push against a bending structure, and the bending structure is capable of engaging the first bridge and the second bridge. Rotation of the handle in the first direction causes the bending structure to engage and bend the first bridge and the second bridge simultaneously to configure the staples from an unrestrained state in which the first pair of legs and the second pair of legs are angled inwardly to a strained state in which the first pair of legs and the second pair of legs are substantially perpendicular to the bridge. Rotation of the handle in the opposing second direction causes the threaded rod and the plunger to move proximally, and the bending structure removes pressure from the first bridge and the second bridge.

In another example, an insertion system includes a body. A first staple includes a first bridge and a first pair of legs each attached to the first bridge at a first elastic hinge region, and a second staple includes a second bridge and a second pair of legs each attached to the second bridge at a second elastic hinge region. The staples are mounted to the body. The insertion system includes a bending structure capable of bending the first bridge and the second bridge. The bending structure bends the first bridge and the second bridge to configure the staples from an unrestrained state in which the first pair of legs and the second pair of legs are angled inwardly to a strained state in which the first pair of legs and the second pair of legs are substantially perpendicular to the bridge.

In another embodiment, the staples are identical.

In another embodiment, the staples have different sizes.

In another embodiment, the staples comprise Nitinol.

In another embodiment, the staples comprise polyether ether ketone (PEEK).

In another embodiment, the body includes a first side and an opposing second side. A first pair of plates are each mounted to the first side of the body by a first proximal pin, and a second pair of plates are each mounted to the second side of the body by a second proximal pin. Each of the first pair of plates includes a first distal pin, and each of the second pair of plates includes a second distal pin. The first staple is mounted on the first distal pins, and the second staple is mounted on the second distal pins.

In another embodiment, each of the first distal pins of the first pair of plates are located under one of the first elastic hinge regions of the first staple, and each of the second distal pins of the second pair of plates are located under one of the second elastic hinge regions of the second staple.

In another embodiment, the bending structure includes a handle moveable in a first direction and an opposing second direction, and the bending structure bends the first bridge and the second bridge to configure the staples from the unrestrained state to the strained state.

In another embodiment, the multi-staple inserter includes a threaded rod having a proximal end and a distal end and a plunger having a proximal end and a distal end. The body includes an internally threaded passage, the threaded rod is configured to mate with the internally threaded passage of the body, and the handle is mounted to the proximal end of the threaded rod.

In another embodiment, the handle rotates, and rotation of the handle in a first direction causes the threaded rod to move distally such that the distal end of the threaded rod pushes against the proximal end of the plunger to translate the plunger distally. The distal end of the plunger applies pressure on the bending structure to bend the bending structure, and the bending structure simultaneously engages and bends the first bridge and the second bridge to bias the first legs and the second legs of the first staple and the second staple outwardly to configure the staples from the unrestrained state to the strained state.

In another embodiment, rotation of the handle in an opposing second direction causes the threaded rod and the plunger to move proximally, and the bending structure simultaneously removes pressure from the first bridge and the second bridge to configure the staples from the unrestrained state to the strained state.

In another embodiment, the threaded rod has a longitudinal axis, and the bending structure has a longitudinal axis. The longitudinal axis of the threaded rod is substantially perpendicular to the longitudinal axis of the bending structure.

In another embodiment, the staples simultaneously move from the strained state to the unrestrained state and from the unrestrained state to the strained state.

In another embodiment, the bending structure has a rectangular cross section and a length, and a bottom surface of the bending structure is capable of engaging and bending the first bridge and the second bridge.

In another embodiment, the bending structure includes a first pin set including a first pin and a second pin extending from a first pin set support arm and configured to support the first staple, and a second pin set including a first pin and a second pin extending from a second pin set support arm and configured to support the second staple. The body supports the support arms, and the staples are released via a release maneuver.

In another embodiment, the staples are released simultaneously via the release maneuver.

In another embodiment, the first pin set support arm includes a first pin set first support arm and a first pin set second support arm both extending from the body, and the first pin and the second pin of the first pin set extends from the first pin set first support arm and the first pin set second support arm, respectively. The second pin set support arm includes a second pin set first support arm and a second pin set second support arm both extending from the body, and the first pin and the second pin of the second pin set extends from the second pin set first support arm the second pin set second support arm, respectively.

In another embodiment, the pins of the first pin set and the pins of the second pin set extend from the first pin set support arm and the second pin set support arm, respectively, in the same direction.

In another embodiment, the release maneuver includes lateral movement of the support arms.

In another embodiment, the bending structure includes a retention member removably positioned between the pins of the first pin set and the pins of the second pin set.

In another embodiment, the release maneuver includes movement of the retention member sufficient to permit release of both the staples and lateral movement of the support arms.

In another embodiment, the pins of the first pin set extend from the first pin set support arm in misaligned directions, and the pins of the second pin set extend from the second pin set support arm in misaligned directions.

In another embodiment, the pins of the first pin set extend from the first pin set support arm in opposite directions and the pins of the second pin set extend from the second pin set support arm in opposite directions.

In another embodiment, the bending structure includes a first pin set including a first pin and a second pin extending from a first pin set support arm, and a second pin set including a first pin and a second pin extending from a second pin set support arm. The bending structure includes a first handle extending from the first pin set support arm, a second handle extending from the second pin set support arm, and the second handle is pivotally attached to the first handle. The first pin set first pin and the second pin set first pin are configured to support the first staple, and the first pin set second pin and the second pin set second pin are configured to support the second staple. The staples are released via a release maneuver.

In another embodiment, the pins of the first pin set and the pins of the second pin set extend from the support arms, respectively, in the same direction.

In another embodiment, the first pin of the first pin set extends in a different direction than the first pin of the second pin set, and the second pin of the first pin set extends in a different direction than the second pin of the second pin set.

In another embodiment, the first pin of the first pin set extends in an opposite direction than the first pin of the second pin set, and the second pin of the first pin set extends in an opposite direction than the second pin of the second pin set.

In another embodiment, the body includes a first body and a second body, and the first body is pivotally coupled to the second body. A first receiver is coupled to the first body and configured to receive the first staple, and a second receiver is coupled to the second body and configured to receive the second staple. The bodies are configured to pivot between a closed position in which the first staple is contained in the first receiver and the second staple is contained in the second receiver and an open position in which the first staple is released from the first receiver and the second staple is released from the second receiver.

In another embodiment, the bending structure includes a restraint member configured to restrain the bodies in the closed position, and the bodies are biased away from each other.

In another embodiment, the first receiver and the second receiver include a first staple receiving opening and a second staple receiving opening, respectively, that face each other such that the staples are prevented from being released in the closed position. The staples are permitted to be released through the staple receiving openings when in the open position.

In another example, a method of inserting at least two staples into a bone includes moving a handle of a multi-staple inserter of an insertion system in a first direction to configure the at least two staples mounted to a body of the multi-staple inserter from an unrestrained state to a strained state to bend a bridge of the at least two staples to move a pair of legs of the at least two staples to be substantially perpendicular to the bridge. The method includes inserting each of the pair of legs of the at least two staples into a set of holes in the bone and releasing the at least two staples from the body of the multi-staple inserter.

In another embodiment, each of the pair of legs are attached to the bridge at a pair of first elastic hinge regions. The method includes mounting each of the pair of elastic hinge regions of the staple on a pair of distal pins that are each mounted to a pair of plates. The pair of plates are each mounted to a side of the body of the multi-staple inserter by a proximal pin.

In another embodiment, each of the pair of distal pins is located under one of the elastic hinge regions of the at least two staples.

In another embodiment, the step of moving the handle includes moving a threaded rod configured to mate with an internally threaded passage of the body of the multi-staple inserter distally such that a distal end of the threaded rod pushes against a proximal end of a plunger to translate the plunger distally. A distal end of the plunger applies pressure on a bending structure to bend the bending structure. The bending structure engages and bends the bridge of the at least two staples to bias the pair of legs of the at least two staples outwardly to configure the at least two staples from the unrestrained state to the strained state.

In another embodiment, the at least two staples simultaneously move from the strained state to the unrestrained state and from the unrestrained state to the strained state.

In another embodiment, the step of removing the at least two staples from the body of the multi-staple inserter includes moving the handle of the multi-staple inserter in a second opposite direction.

In another example, an interfragmentary drill guide includes a body including at least one hole to receive a drill that forms a screw passage having a trajectory in a bone. The screw passage receives an interfragmentary screw that crosses a fracture line of the bone. The interfragmentary drill guide includes two slots that each receive a tube of a drill guide used to form a drill passage in the bone that each receive a leg of a staple. The drill passages are located on opposing sides of the fracture line of the bone. The trajectory of the interfragmentary screw does not intersect the legs of the staple.

In another embodiment, the interfragmentary drill guide includes a handle attached to the body.

In another embodiment, a bottom surface of the body includes an elongated recess, and a bridge of the staple is received in the elongated recess to locate the body relative to the staple.

In another embodiment, an upper surface of the body includes a plurality of staple markings including a central marking that extends from a front face of the body and between the two slots and a pair of staple markings each substantially parallel to the central marking. Each of the staple markings are equidistant from the central marking, and the pair of staple markings align with ends of a bridge of the staple to provide a visual indication of alignment of the interfragmentary drill guide with the staple.

In another embodiment, the handle and the body are a single, monolithic, unitary component.

In another example, a method of compressing a fracture includes aligning a body of an interfragmentary drill guide relative to a bone such that each of two slots and each of two holes of the body of the interfragmentary drill guide are located on opposing sides of a fracture line of the bone. The method includes positioning a tube of a drill guide in each of the two slots of the interfragmentary drill guide to form a drill passage each located on opposing sides of the facture line of the bone that each receive a leg of a staple and forming a screw passage through at least one hole of the body of the interfragmentary drill guide. The screw passage has a trajectory that crosses the fracture line of the bone that does not intersect the legs of the staple.

In another embodiment, the step of aligning the body of the interfragmentary drill guide includes receiving a bridge of the staple in an elongated recess on a bottom surface of the interfragmentary drill guide.

In another embodiment, the step of aligning the body of the interfragmentary drill guide includes aligning a pair of staple markings on an upper surface of the body of the interfragmentary drill guide with ends of a bridge of the staple to provide a visual indication of alignment of the interfragmentary drill guide with the staple.

Figure 2:
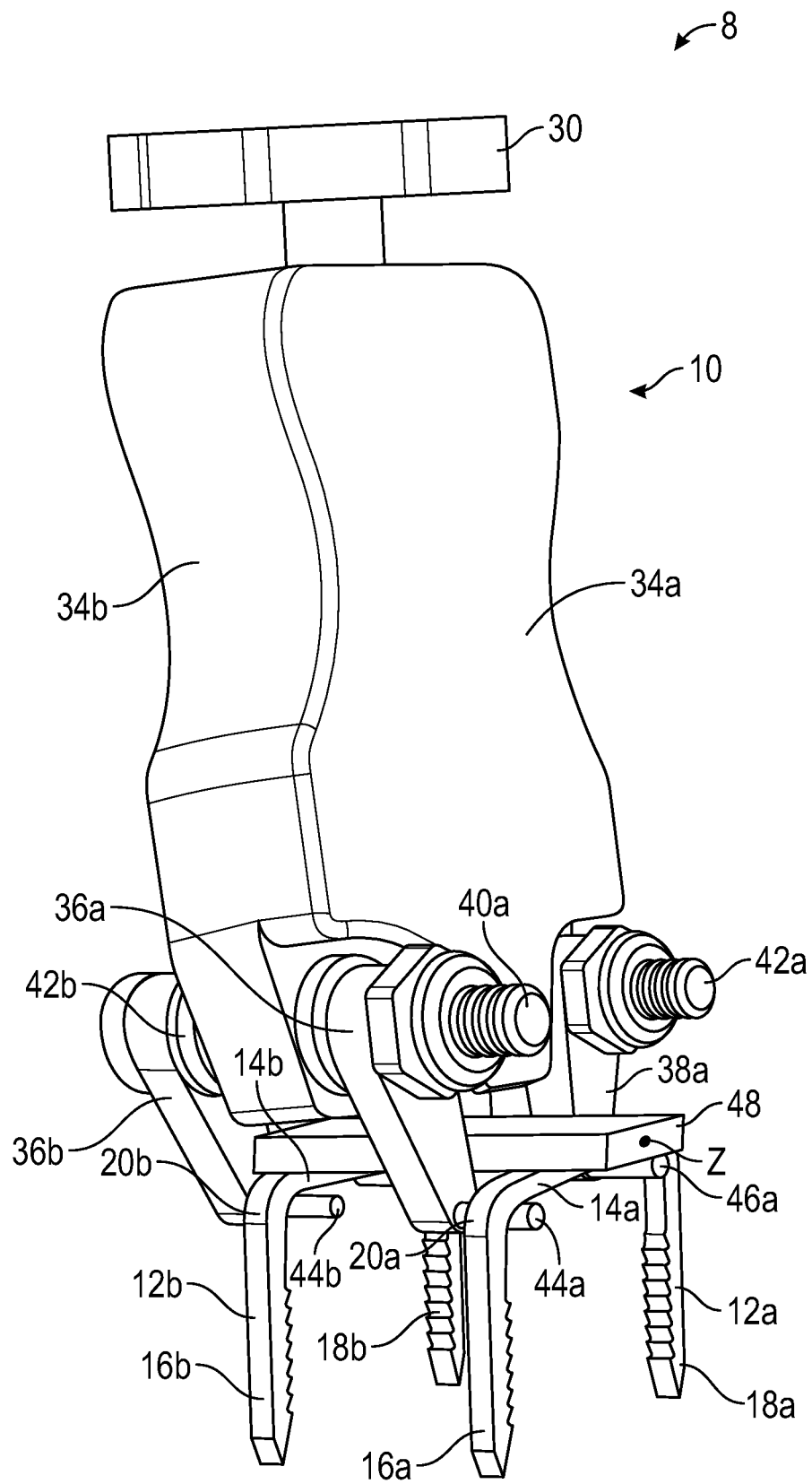
FIG. 2 illustrates another perspective view of the insertion system.
Figure 3:
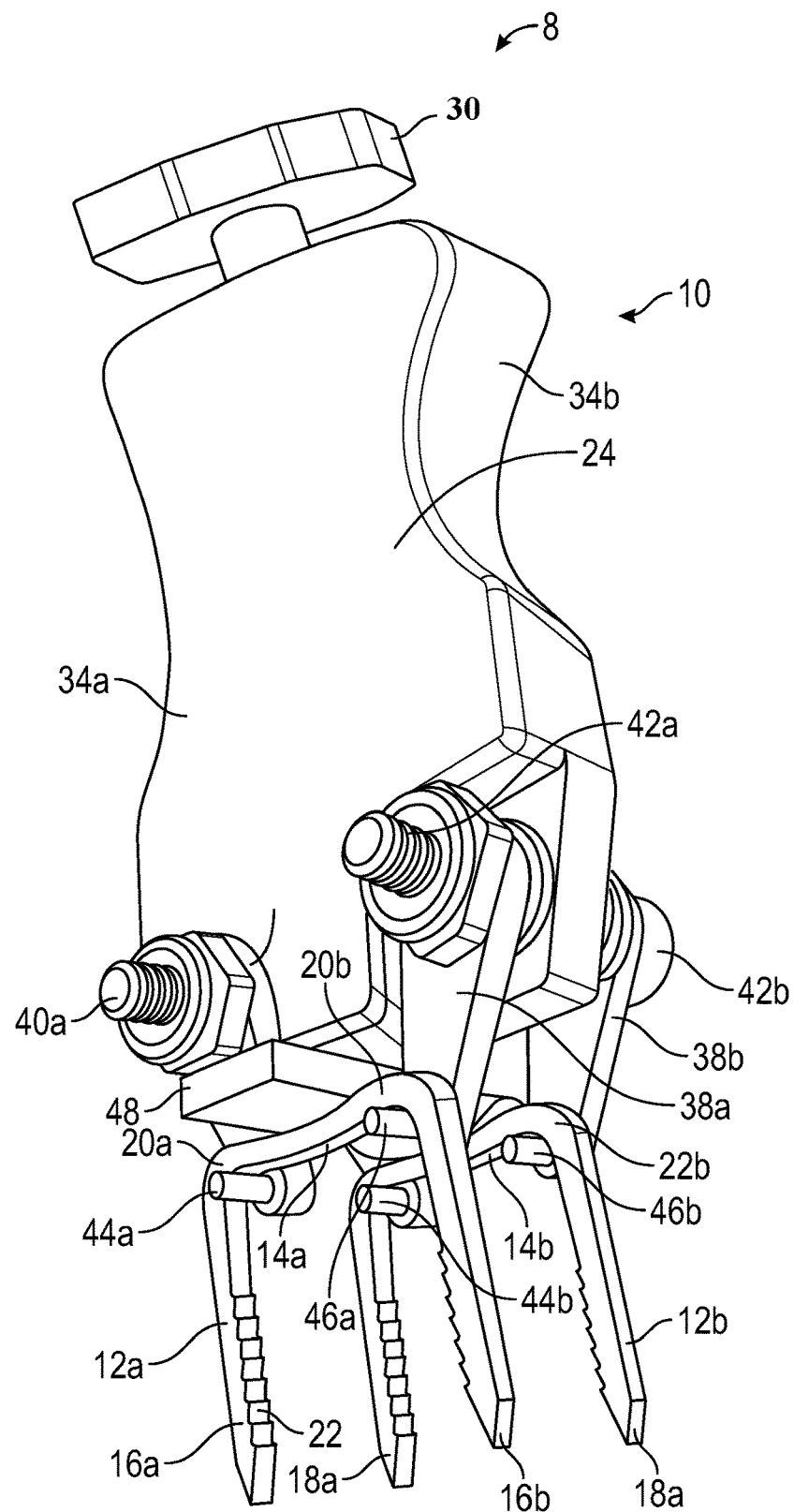
FIG. 3 illustrates another perspective view of the insertion system.

FIGS. 1 to 3 illustrate an insertion system 8 including a multi-staple inserter 10 that constrains and holds a plurality of staples 12 in a strained state for implantation across a fracture line 100 in a fractured bone 98. The staples 12 can bring bone fragments 98a and 98b into close proximity with each other, generating a compressive load between the bone fragments 98a and 98b of the fractured bone 98 across the fracture line 100 (shown in FIG. 29) and maintaining a compressive load across the fracture line 100 during healing.

In an example, the multi-staple inserter 10 constrains and holds two identical staples 12a and 12b. The two staples 12a and 12b are made of a shape memory material (e.g., a material capable of exhibiting superelasticity and/or a temperature-induced shape change). In an example, the staples 12a and 12b are made of a metal alloy, such as Nitinol. In another example, the staples 12a and 12b are made of a polymer, such as polyether ether ketone (PEEK). In an example, the two staples 12a and 12b have different sizes.

Figure 4:
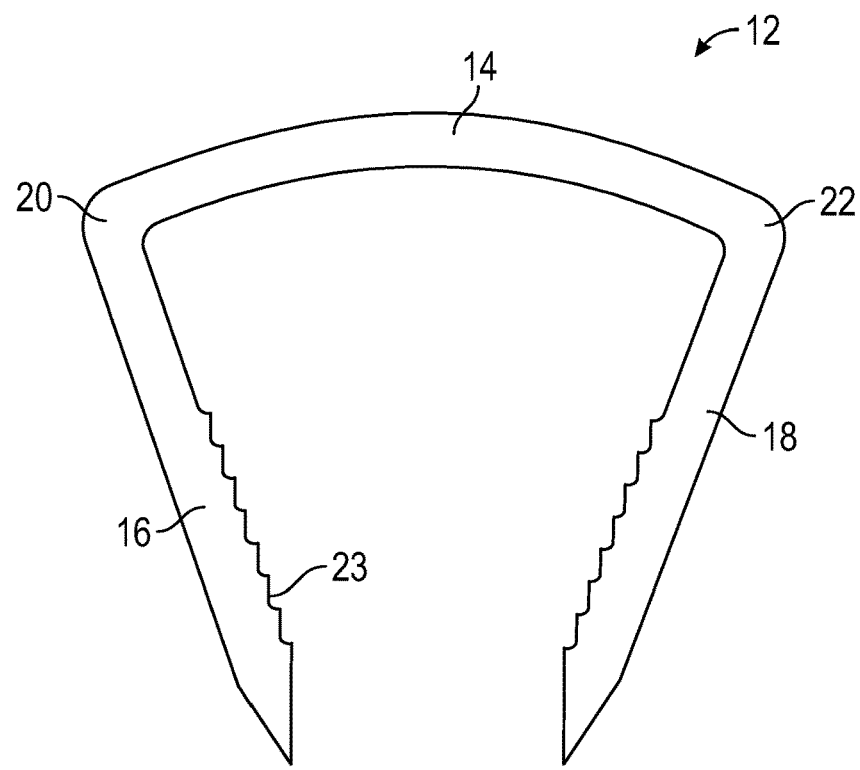
FIG. 4 illustrates a front view of a staple in an unrestrained state.
Figure 5:
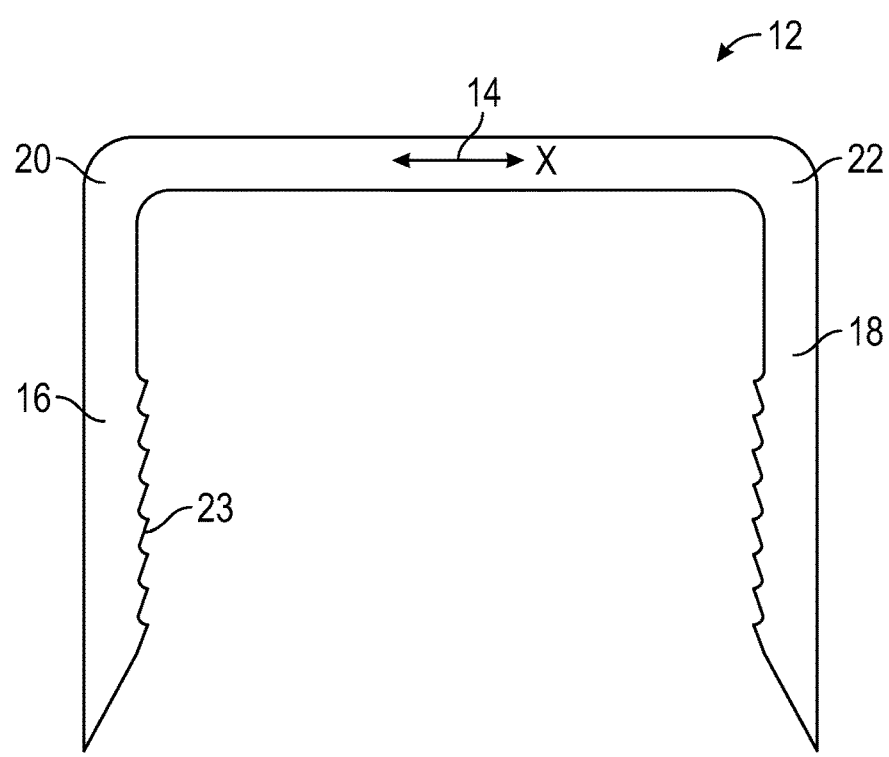
FIG. 5 illustrates a front view of the staple in a strained state.

As shown in FIGS. 4 and 5, the staples 12a and 12b includes an elastic bridge 14a and 14b, respectively. The first staple 12a includes two elastic legs 16a and 18a, and the second staple 12b includes two elastic legs 16b and 18b. The legs 16a and 18a of the first staple 12a meet the bridge 14a at elastic curved hinge regions 20a and 22a, respectively, and the legs 16b and 18b of the second staple 12b meet the bridge 14b at elastic curved hinge region 22b and 22b, respectively. The legs 16a, 16b, 18a, and 18b can have barbed teeth 23 to assist the staples 12a and 12b in gripping the fractured bone 98 after implantation and prevent removal.

As shown in FIG. 4, in an unrestrained state, the bridges 14a and 14b of the staples 12a and 12b are bowed upwardly, and the legs 16a, 16b, 18a, 18b of the staples 12a and 12b are elastically pivoted inwardly at the hinge regions 20a, 20b, 22a, and 22b. In an example, the legs 16a, 16b, 18a, 18b of the staples 12a and 12b are each at an angle of less than 90° relative to a longitudinal axis X of the bridges 14a and 14b. In another example, the legs 16a, 16b, 18a, 18b of the staple 12a and 12b extend at an angle of about 65° relative to the longitudinal axis X of the bridges 14a and 14b.

As shown in FIG. 5, the strained state, the multi-staple inserter 10 simultaneously elastically reversibly bends the bridges 14a and 14b of the staples 12a and 12b to be nearly linear or bent inwardly. The legs 16a, 16b, 18a, and 18b of the staples 12a and 12b are reversibly pivoted at elastic hinge regions 20a, 20b, 22a, and 22b to be substantially perpendicular to the longitudinal axis X of the bridges 14a and 14b, allowing the legs 16a, 16b, 18a, 18b of the staples 12a and 12b to be inserted across the fracture line 100. Each of the legs 16a and 18a of the first staple 12a are connected to one end of the bridge 14a at one of the elastic hinge regions 20a and 22a, respectively, and each of the legs 16b and 18b of the second staple 12b are connected to one end of the bridge 14a at one of the elastic hinge regions 20b and 22b, respectively.

Figure 6:
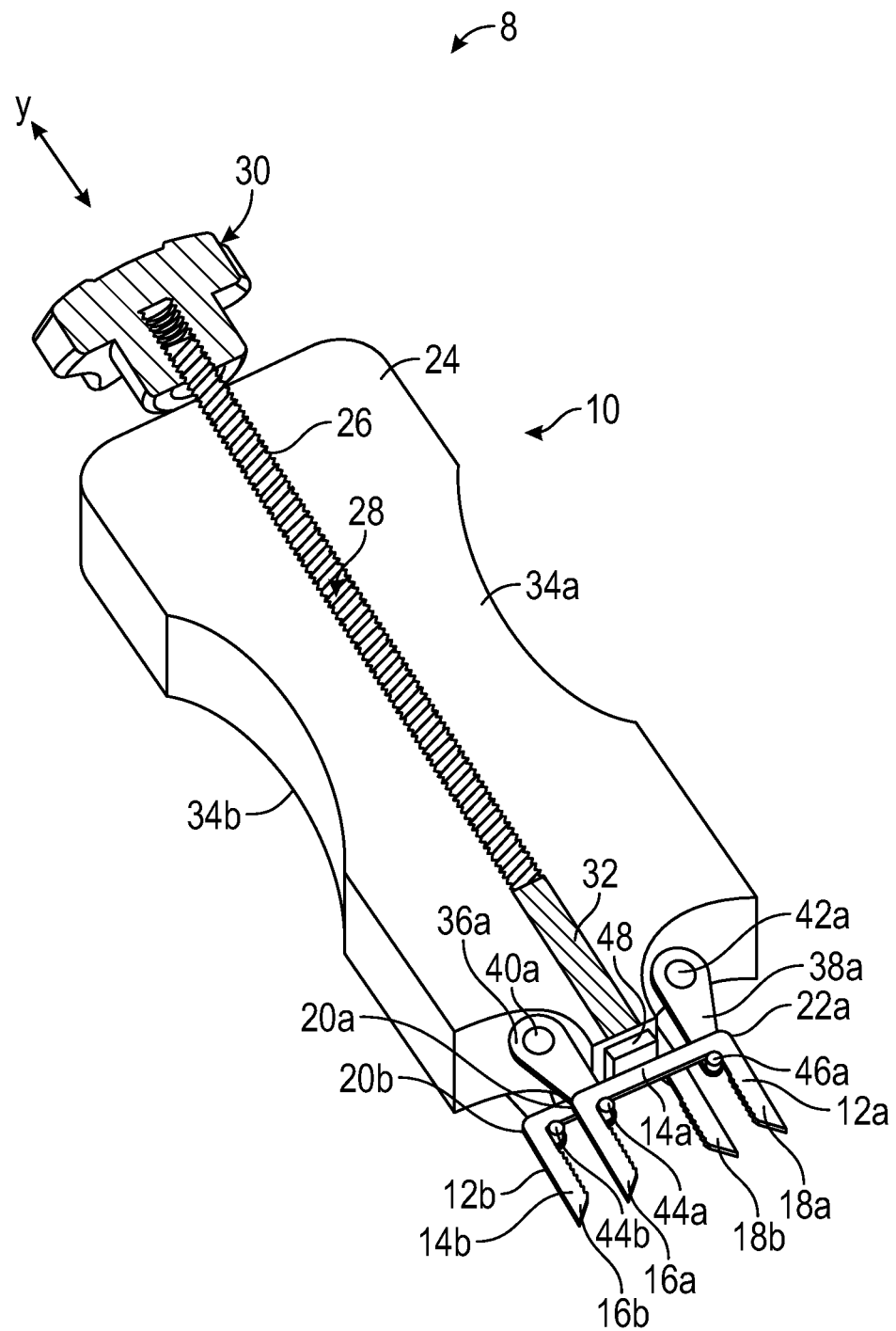
FIG. 6 illustrates a front view of the insertion system including a staple in a strained state.

As shown in FIG. 6, the multi-staple inserter 10 includes a body 24 having an internal threaded region 26. A threaded rod 28 has a longitudinal axis Y and is configured to mate with the internal threaded region 26. In an example, a proximal end of the threaded rod 28 mates with an internal threaded region in the handle 30 to secure the handle 30 to the threaded rod 28. By selectively rotating the handle 30 in a first direction to selectively rotate the threaded rod 28, the threads of the threaded rod 28 engage the internal threaded region 26 of the body 24, distally advancing the threaded rod 28. As the threaded rod 28 translates distally, a distal end of the threaded rod 28 pushes against a proximal end of a plunger 32. In another example, the rod is not threaded, and the rod translates by pushing on the handle 30 in a distal direction.

The body 24 includes a first side 34a and an opposing second side 34b. A pair of plates 36a and 38a are each mounted to the first side 34a of the multi-staple inserter 10, and a pair of plates 36b and 38b are each mounted to the second side 34b of the multi-staple inserter 10. In an example, the plates 36a and 38a are each pivotally mounted to the first side 34a of the multi-staple inserter 10, and plates 36b and 38b are each pivotally mounted to the second side 34b of the multi-staple inserter 10. In another example, the plates 36a and 38a are each fixed to the first side 34a of the multi-staple inserter 10, and plates 36b and 38b are each fixed to the second side 34b of the multi-staple inserter 10.

In an example, the plates 36a, 36b, 38a and 38b are mounted at a distal end of the body 24. One proximal end of each plate 36a, 36b, 38a, and 38b is mounted to the body 24 by a respective proximal pin 40a, 40b, 42b, and 42b, and an opposing distal end of each plate 36a, 36b, 38a, and 38b includes a respective distal pin 44a, 44b, 46a, and 46b mounted thereon. The staple 12a is releasably mounted to the pair of plates 36a and 38a on the first side 34a of the multi-staple inserter 10, and the staple 12b is releasably mounted to the pair of plates 36b and 38b on the second side 34b of the multi-staple inserter 10. In an example, the staples 12a and 12b are mounted such that the distal pins 44a, 44b, 46a, and 46b, respectively, are located under the elastic hinge regions 20a, 20b, 22a, and 22b, respectively. In an example, the distal pins 44a, 44b, 46a, and 46b extend from the respective plates 36a, 36b, 38a, and 38b in a common direction. In an example, the plates 36a, 36b, 38a, and 38b are pivotally mounted to the body 24.

In another example, the staples 12a and 12b includes a hole (not shown) in each of the hinge regions 20a, 20b, 22a, and 22b. The distal pins 44a, 44b, 46a, and 46b are each received in one of the holes in the hinge regions 20a, 20b, 22a, and 22b, respectively, to mount the staples 12a and 12b to the body 24. In another example, the holes can be external to the staples 12a and 12b and located in a lobe or an ear located proximate to the hinge regions 20a, 20b, 22a, and 22b.

When the handle 30 is moved, the distal end of the threaded rod 28 pushes against the proximal end of the plunger 32, and the plunger 32 translates distally and engages a bending structure 48 to transfer force to the staples 12a and 12b. In an example, the bending structure 48 is a beam having a rectangular cross-section and a length and extends over and engages the bridges 14a and 14b of both the respective staples 12a and 12b. In an example, the bending structure 48 is located outside the body 24. In an example, as the plunger 32 moves distally and provides pressure on the bending structure 48, the bending structure 48 provides simultaneous pressure on an upper surface of the bridges 14a and 14b of the staples 12a and 12b, respectively. In an example, a longitudinal axis Z of the bending structure 48 is substantially perpendicular to the longitudinal axis Y of the threaded rod 28.

In another example, the bending structure 48 is located inside the body 24. As the handle 30 is moved, the threaded rod 28 moves distally towards the staples 12a and 12b. The threaded rod 28 engages an upper surface of the bending structure 48 inside the body 24. Two plungers are attached to a lower surface of the bending structure 48, and each plunger is associated with one of the staples 12a and 12b. As the bending structure 48 and the plungers move distally, each plunger engages the bridge 14a and 14b of one of the staples 12a and 12b, respectively.

In another example, the multi-staple inserter 10 does not include a plunger 32 or a bending structure 48, and the threaded rod 28 engages the plungers directly. In this example, the threaded rod 28 has a size large enough to engage both of the plungers at the same time. In this example, the threaded rod 28 acts as the plunger.

In an example, the plunger 32 and the bending structure 48 are a single integral monolithic component. In another example, the threaded rod 28, the plunger 32, and the bending structure 48 are a single, integral, monolithic component.

Figure 7:
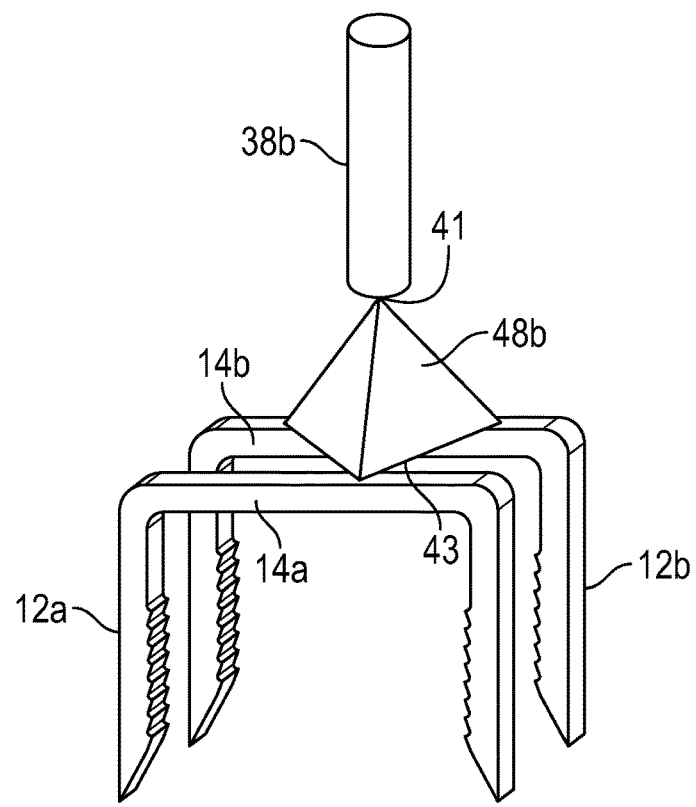
FIG. 7 illustrates a perspective view of a portion of an insertion system including a bending structure shaped as a pyramid.

In another example shown in FIG. 7, the bending structure 48b is a pyramid. The plunger 38b engages an upper apex 41 of the pyramidal bending structure 48b, and a bottom surface 43 of the bending structure 48b engages both the bridges 14a and 14*b* of the staples 12*a* and 12*b*, respectively. The bending structure 48*b* can also be used in any of the examples described above.

Figure 8:
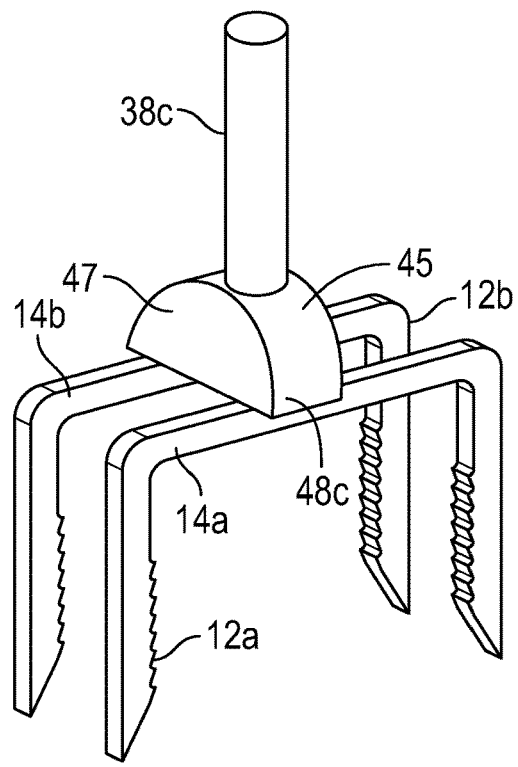
FIG. 8 illustrates a perspective view of a portion of an insertion system including a bending structure shaped as a half circle.

In another example shown in FIG. 8, the bending structure 48*c* is semi-circular in shape. In this example, the plunger 38*c* engages a curved surface 45 of the bending structure 48*c*. A flat portion 47 of the plunger 38*c* defined by the diameter of the semi-circular bending structure 48*c* engages both the bridges 14*a* and 14*b* of the staples 12*a* and 12*b*, respectively. The bending structure 48*c* can also be used in any of the examples described above.

Figure 9:
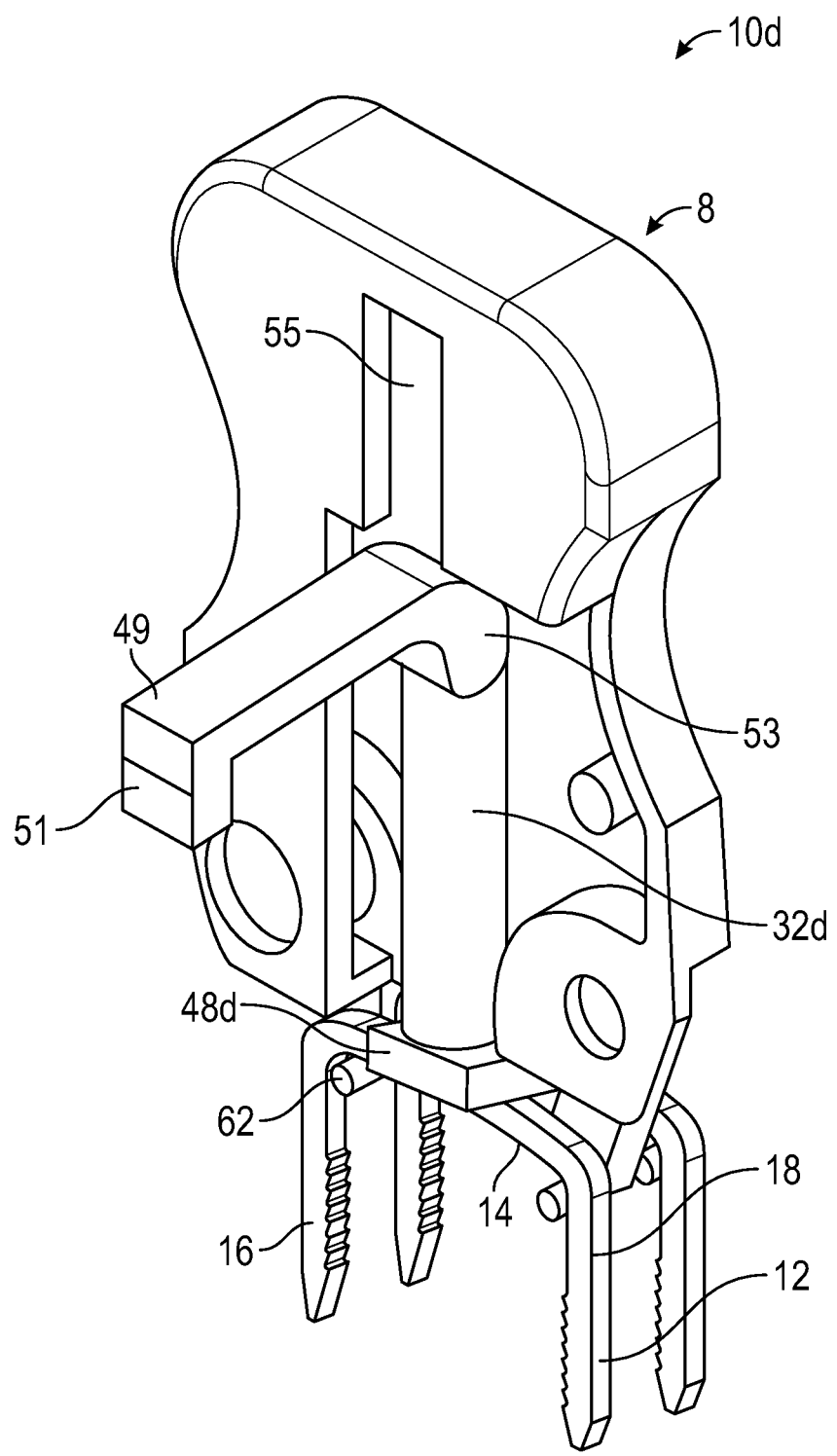
FIG. 9 illustrates a perspective view of an insertion system including a lever.

In another example shown in FIG. 9, the multi-staple inserter 10 does not include a handle, a threaded rod, and a threaded passage. In this example, the multi-staple inserter 10 includes a lever 49. The lever 49 includes a gripping portion 51 at one end and a cam 53 at an opposing end. In an example, the cam 53 interfaces with a plunger 32*d* that engages the bending structure 48*d* that engages the bridges 14*a* and 14*b* of the respective staples 12*a* and 12*b*. In another example, the cam 53 interfaces with a bending structure 48*d* that engages the bridges 14*a* and 14*b* of the respective staples 12*a* and 12*b*. In another example, the cam 53 engages a plunger 32*b* that engages both the bridges 14*a* and 14*b* of the respective staples 12*a* and 12*b*. When the lever 49 is removed from a recess 55 in the body 62 and pivoted about a fulcrum by selectively moving the gripping portion 51 of the lever 49, the mechanical advantage of the lever 49 applies a force to the plunger 32*d* through the cam 53, advancing the plunger 32*d* and/or the bending structure 48 distally to change the staples 12*a* and 12*b* from the unrestrained state to the strained state.

The bending structure 48 applies pressure on the upper surface of the bridges 14*a* and 14*b* of the staples 12*a* and 12*b* to bend the bridges 14*a* and 14*b* into a more linear configuration or a concave configuration so that the staples 12*a* and 12*b* are in the strained state. The elastic hinge regions 20*a*, 20*b*, 22*a*, and 22*b* of the staples 12*a* and 12*b* bend about the distal pins 44*a*, 44*b*, 46*a*, and 46*b* of the plates 36*a*, 36*b*, 38*a*, and 38*b* to pivot the legs 16*a*, 16*b*, 18*a*, 18*b* outwardly and spread the legs 16*a*, 16*b*, 18*a*, 18*b* of the staples 12*a* and 12*b* apart. In an example, the legs 16*a*, 16*b*, 18*a*, 18*b* are oriented to be generally perpendicular to the elastic bridges 14*a* and 14*b* when the staples 12*a* and 12*b* are in the strained state.

The force imparted by turning the handle 30 of the multi-staple inserter 10 is split by the bending structure 48 between the two staples 12*a* and 12*b*, allowing the legs 16*a*, 16*b*, 18*a*, and 18*b* of the staples 12*a* and 12*b* to open the same distance simultaneously so that the staples 12*a* and 12*b* can be delivered at the same time, saving space and time, and adding precision during implantation.

Figure 10:
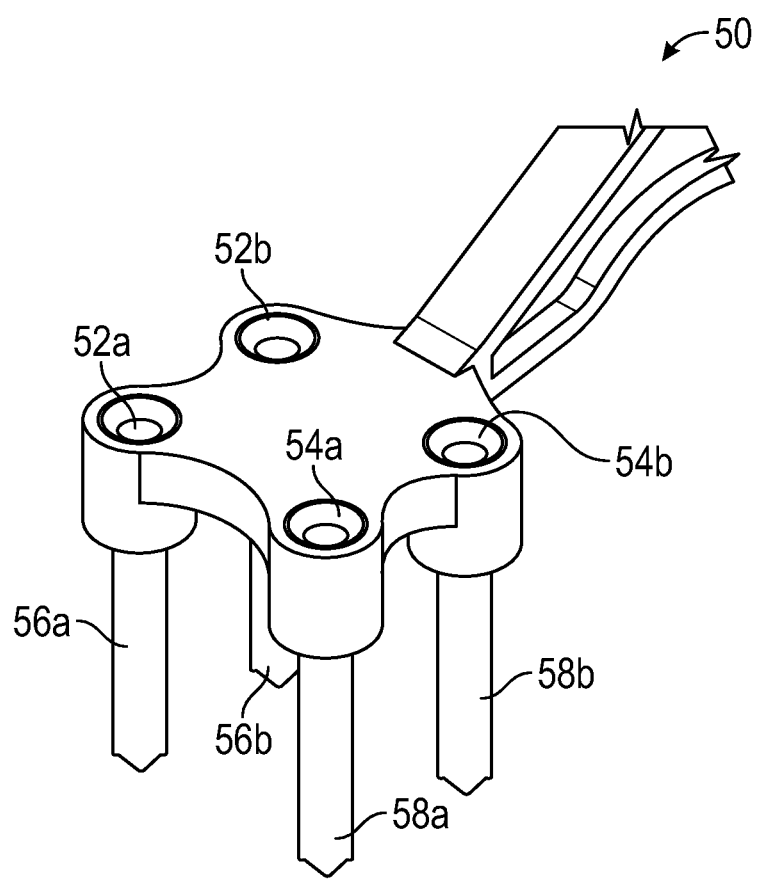
FIG. 10 illustrates a partial proportional view of a drill guide.
Figure 11:
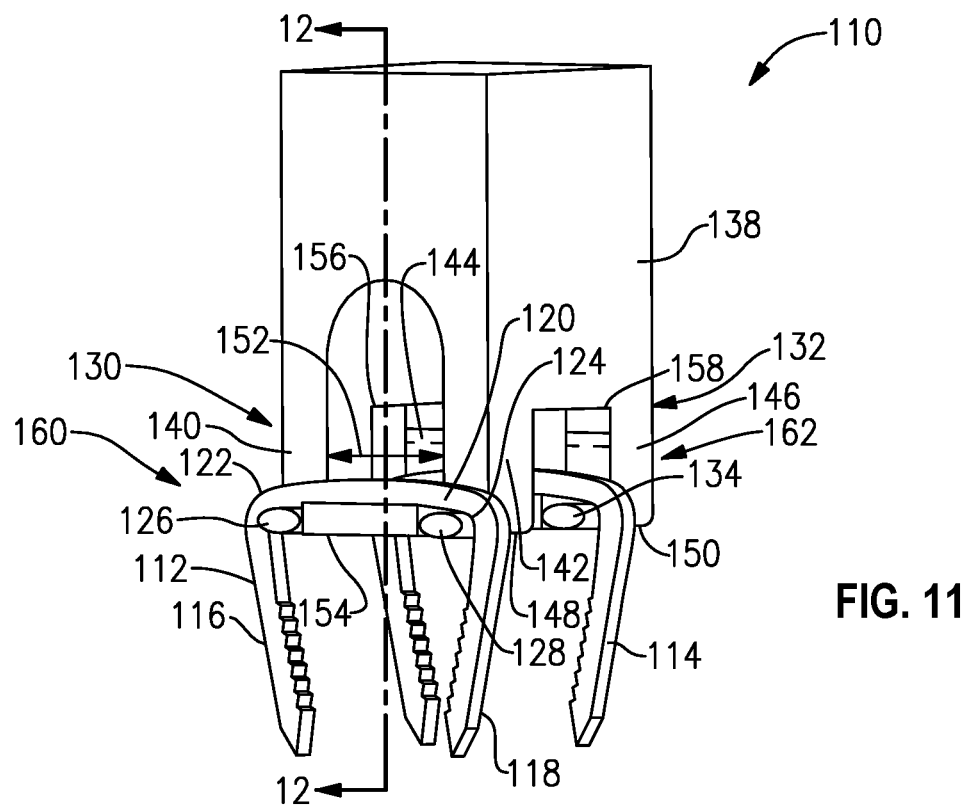
FIG. 11 illustrates a perspective view of a multiple staple delivery device with a retention member for restraining a first staple and a second staple held in position for release.
Figure 12:
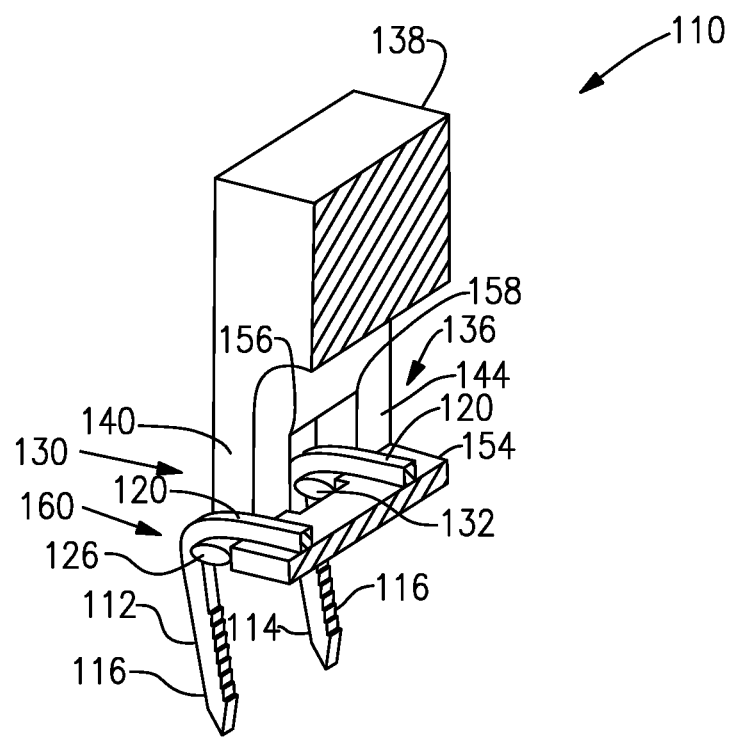
FIG. 12 illustrates a cross-sectional view of the multiple staple delivery device of FIG. 11 taken along section line 12-12.

The multi-staple inserter 10 can strain and hold the staples 12*a* and 12*b* in the strained state prior to implantation, and then insert the staples 12*a* and 12*b* into pre-drilled holes in fracture site (described below with respect to FIG. 10). Upon insertion of the strained staples 12*a* and 12*b* into the fracture site, the multi-staple inserter 10 removes constraint from the staples 12*a* and 12*b*. Once inserted, the bridges 14*a* and 14*b* of each of the staples 12*a* and 12*b* span across the fracture line 100. The staples 12*a* and 12*b* attempt to return to the original unrestrained state, creating and maintaining a compressive load across the fracture line 100 of the fractured bone 98 during healing.

Prior to implantation, a fracture site between bone fragments of a bone is prepared. As shown in FIG. 10, a drill guide 50 includes a first of set holes 52*a* and 54*a* for the first staple 12*a* and a second set of holes 52*b* and 54*b* for the second staple 12*b*. A drill tube 56*a*, 58*a*, 56*b*, 58*b* extends from each of the holes 52*a*, 54*a*, 52*b*, and 52*b*, respectively. The drill guide 50 is placed on the fractured bone 98 such that one set of drill tubes 56*a* and 56*b* is located on one side of the fracture line 100, and the other set of drill tubes 58*a* and 58*b* is located on the other side of the fracture line 100. A drill (not shown) is used to drill four pre-drilled holes using the drill tubes 56*a*, 58*a*, 56*b*, 58*b* for guidance. The pre-drilled holes are a predetermined distance apart to accommodate the legs 16*a*, 16*b*, 18*a*, 18*b* of the staples 12*a* and 12*b*. The drill guide 50 is then removed from the fractured bone 98.

After the staples 12*a* and 12*b* are mounted to the distal pins 44*a*, 44*b*, 46*a*, and 46*b* and in the strained state, the legs 16*a*, 16*b*, 18*a*, 18*b* of the staples 12*a* and 12*b* are placed into the pre-drilled holes by the multi-staple inserter 10. The legs 16*a* and 18*a* of the staple 12*a* are received in the holes formed by the drill that is guided by the drill tubes 56*a* and 58*a*, and the legs 16*b* and 18*b* of the staple 12*b* are received in the holes formed by the drill that is guided by the drill tubes 56*b* and 58*b*.

The handle 30 is turned in a second opposite direction, and the staples 12*a* and 12*b* are released from the distal pins 44*a*, 44*b*, 46*a*, and 46*b* of the multi-staple inserter 10, sliding the staples 12*a* and 12*b* off of the distal pins 44*a*, 44*b*, 46*a*, and 46*b*. Once the staples 12*a* and 12*b* are released from the multi-staple inserter 10, the legs 16*a*, 16*b*, 18*a*, 18*b* attempt to bias inwardly to return the staples 12*a* and 12*b* to the unrestrained state. The bent elastic bridges 14*a* and 14*b* and the straight legs 16*a*, 16*b*, 18*a*, 18*b* of the staples 12*a* and 12*b* attempt to return to the unrestrained state, applying compression across the fracture line 100 of the fractured bone 98.

The multi-staple inserter 10 can also be used to remove the staples 12*a* and 12*b* from a bone. The distal pins 44*a*, 44*b*, 46*a*, and 46*b* of the multi-staple inserter 10 reengage the staples 12*a* and 12*b* under the respective hinge regions 20*a*, 20*b*, 22*a*, and 22*b*. The handle 30 is turned in the first direction to translate the threaded rod 28 and the plunger 32 proximally, applying pressure to the bending structure 48. The bending structure 48 applies pressure to the upper surfaces of the bridges 14*a* and 14*b* to bend the bridges 14 and 14*b* and bias the legs 16*a*, 16*b*, 18*a*, and 18*b* outwardly. As the staples 12*a* and 12*b* attempt to return to the strained state, the staples 12*a* and 12*b* can be removed from the bone.

Although a multi-staple inserter 10 that holds and installs two identical staples 12*a* and 12*b* is illustrated and described, the multi-staple inserter 10 can hold any number of identical staples 12. In another example, the force can be split among a plurality of staples 12 of multiple sizes. In this example, the distance the plunger 32 travels is distributed unevenly so that the staples 12 open at different rates or at different distances, allowing staples 12 with different opening requirements to be delivered together. This can be adjusted to deliver staples 12 of any size or configuration, such as multi-legged staples and step-staples. In another example, the staples 12*a* and 12*b* are not identical. For example, the bridges 14*a* and 14*b* of the respective staples 12*a* and 12*b* could have different widths. In another example, the legs 16*a* and 18*a* of the staple 12*a* or the legs 16*b* and 18*b* of the staple 12*b* could have different lengths on the same staple 12*a* or 12*b* or different lengths than the other staple. In another example, the staples 12*a* and 12*b* have a different number of legs. Additionally, although the staples 12*a* and 12*b* have been described as repairing a fractured bone 98, the staples 12 can be used to attach soft tissue to bone (for example, to attach a rotator cuff to bone). In another example, the staples 12 can be used to fuse a joint.

The method can also include mounting each of the first elastic hinge regions 20a and 22a of the first staple 12a on one of the respective first distal pins 44a and 46a that are each mounted to one of the respective first pair of plates 36a and 38a and mounting each of the second elastic hinge regions 20b and 22b of the second staple 12b on one of the respective second distal pins 44b and 46b that are each mounted to one of the respective second pair of plates 36b and 38b. The first pair of plates 36a and 38a are mounted to a first side 34a of the body 24 by the first proximal pins 40a and 42a, and the second pair of plates 36b and 38b are mounted to the second side 34b of the body 24 by the second proximal pins 40b and 42b.

Each of the first distal pins 44a and 46a of the first pair of plates 36a and 38a, respectively, are located under one of the first elastic hinge regions 20a and 22a, respectively, of the first staple 12a, and each of the second distal pins 44b and 46b of the second pair of plates 36b and 38b, respectively, are located under one of the second elastic hinge regions 20b and 22b, respectively, of the second staple 12b. The staples 12a and 12b can simultaneously move from the strained state to the unrestrained state and from the unrestrained state to the strained state. The step of removing the staples 12a and 12b from the body 62 of the multi-staple inserter 10 includes moving the handle 30 of the multi-staple inserter 10 in a second opposite direction.

A method of inserting the staples 12a and 12b into the fractured bone 98 includes moving the handle 30 of the multi-staple inserter 10 of the insertion system 8 in a first direction to configure the staples 12a and 12b mounted to the multi-staple inserter 10 from the unrestrained state to the strained state. Moving the handle 30 in the first direction bends the first bridge 14a of the first staple 12a to move the first pair of legs 16a and 18a to be substantially perpendicular to the first bridge 14a and bends the second bridge 14b of the second staple 12b to move the second pair of legs 16b and 18b to be substantially perpendicular to the second bridge 14a.

The method includes inserting each of the first pair of legs 16a and 18a of the first staple 12a into one of the first set of holes in the fractured bone 98 and inserting each of the second pair of legs 16b and 18b of the second staple 12b into one of the second set of holes in the fractured bone 98. The method also includes releasing the staples 12a and 12b from the multi-staple inserter 10 of the insertion system 8, allowing the staples 12a and 12b to attempt to return to the unrestrained state in which the first pair of legs 16a and 18a and the second pair of legs 16b and 18b are angled inwardly. The staples 12a and 12b can be released simultaneously or can be released in an ordered manner (e.g., the first staple 12a is released and then the second staple 12b is released).

FIGS. 11 to 19 illustrate a multiple staple delivery device 110 configured to deliver a first staple 112 and a second staple 114 via a release maneuver. In one example, more than two staples can be employed. In one example, the staples 112 and 114 can be formed from a shape memory material. In one example, the staples 112 and 114 are made of Nitinol.

The multiple staple delivery device 110 can position the staples 112 and 114 adjacent to each other to be positioned into a patient and released via a release maneuver. In one example, the multiple staple delivery device 110 can be configured to deliver and release the staples 112 and 114 simultaneously via the release maneuver. The release maneuver can include one or more steps. The release maneuver can be lateral movement, rotary movement, movement of a retention member sufficient to permit release of both the staples 112 and 114, lateral movement, removal of a restraint member, or any type of movement.

The staples 112 and 114 each have a first leg 116, a second leg 118, and a bridge 120. The legs 116 and 118 meet the bridge 120 at elastic hinge regions 122 and 124, respectively. The legs 116 and 118 are generally converging in a relaxed state. The legs 116 and 118 can be opened to be in a generally parallel position and retained within the multiple staple delivery device 110 where the legs 116 and 118 are under bending stress. The multiple staple delivery device 110 therefore restrains the legs 116 and 118 in a generally parallel position before release. The forces exerted on the multiple staple delivery device 110 by the legs 116 and 118 of the staples 112 and 114 assists in keeping the staples 112 and 114 in place in the multiple staple delivery device 110.

As shown in FIGS. 11 to 14, in one example, the multiple staple delivery device 110 can include a first pin set 160 formed by a first pin 126 and a second pin 128 extending from one or more first support arm 130. The first pin set 160 can be configured to support one or more first staples 112. The multiple staple delivery device 110 can include a second pin set 162 formed by a first pin 132 and a second pin 134 extending from one or more second support arm 136. The second pin set 162 can be configured to support one or more second staples 114. The multiple staple delivery device 110 can include a body 138 supporting the first support arm 130 and the second support arm 136.

The first support arm 130 can include a first arm portion 140 and a second arm portion 142 extending from the body 138. The first pin 126 of the first pin set 160 can extend from the first arm portion 140, and the second pin 128 of the first pin set 160 can extend from the second arm portion 142. The second support arm 136 can include a first arm portion 144 and a second arm portion 146 extending from the body 138. The first pin 132 of the second pin set 162 extends from the first arm portion 144, and the second pin 134 of the second pin set 162 extends from the second arm portion 146.

In one example, the pins 126 and 128 of the first pin set 160 and the pins 132 and 134 of the second pin set 162 can extend from the first support arm 130 and the second support arm 136, respectively, in the same direction. In one example, one or more of the pins 126 and 128 of the first pin set 160 and the pins 132 and 134 of the second pin set 162 can be aligned with each other. In one example, all of the pins 126 and 128 of the first pin set 160 and the pins 132 and 134 of the second pin set 162 are aligned with each other. One or more of the pins 126 and 128 of the first pin set 160 and the pins 132 and 134 of the second pin set 162 can extend substantially perpendicularly from the first support arm 130 and the second support arm 136, respectively. In one example, all of the pins 126 and 128 of the first pin set 160 and the pins 132 and 134 of the second pin set 162 can extend orthogonally from the first support arm 130 and the second support arm 136, respectively. One or more of the pins 126 and 128 of the first pin set 160 can extend from distal ends 148 of the first support arm 130, and one or more of the pins 132 and 134 of the second pin set 162 can extend from distal ends 150 of the second support arm 136.

A lateral spacing 152 of the pins 126 and 128 of the first pin set 160 can be such to adequately support at least one staple, such as one or more first staple 112. In one example, the lateral spacing 152 of the pins 126 and 128 of the first pin set 160 can be such that the pins 126 and 128 support the first staple 112 at the hinge regions 122 and 124, respectively. Similarly, a lateral spacing 152 of the pins 132 and 134 of the second pin set 162 can be such to adequately support at least one staple, such as one or more second staples 114. In one example, the lateral spacing 152 of the pins 132 and 134 of the second pin set 162 can be such that the pins 132 and 134 support the second staple 114 at the hinge regions 122 and 124, respectively.

Figure 14:
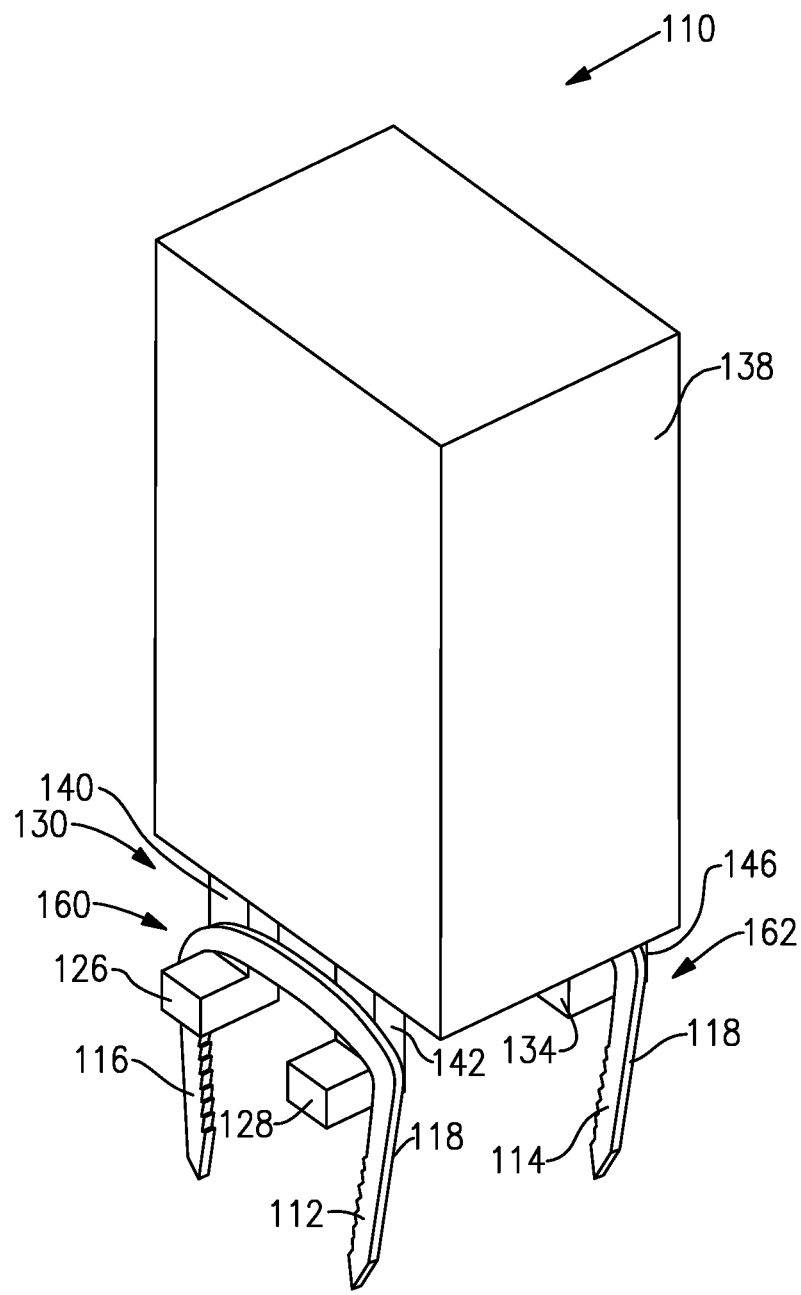
FIG. 14 illustrates a perspective view of another embodiment of the multiple staple delivery device including the pins of the first pin set and the pins of the second pin set extending from the first pin set support arm and the second pin set support arm, respectively, in the same direction.

The pins 126 and 128 of the first pin set 160 and the pins 132 and 134 of the second pin set 162 extend in the same general direction. The staples 112 and 114 are restrained and can be released via a release maneuver. As shown in FIG. 14, the release maneuver used to release the staples 112 and 114 can be a lateral movement of the first support arm 130 and the second support arm 136. In one example, the release maneuver can entail a lateral movement of the body 138 from which the support arms 130 and 136 extend. More specifically, the release maneuver can entail a lateral movement of the body 138 from which the arm portions 140 and 142 of the first support arm 130 and the arms portions 144 and 146 of the second support arm 136 extend.

The multiple staple delivery device 110 can include a retention member 154 removably positioned between the pins 126 and 128 of the first pin set 160. The retention member 154 can be removably positioned between the pins 132 and 134 of the second pin set 162. The retention member 154 can be any appropriate size and shape to prevent the staples 112 and 114 from being prematurely released from the pins 126 and 128 of the first pin set 160 and the pins 132 and 134 of the second pin set 162. In one example, the retention member 154 can be an elongated, flat, plate member. In other examples, the retention member 154 can have other appropriate configurations.

The retention member 154 can be in contact with the arm portions 140 and 142 of the first support arm 130 or the pins 126 and 128 of the first pin set 160, or both. The retention member 154 can be in contact the arms portions 144 and 146 of the second support arm 136 or the pins 132 and 134 of the second pin set 162, or both. The staples 112 and 114 restrained by the first pin set 160 and the second pin set 162 can be released via a release maneuver that includes first moving the retention member 154 sufficient to permit release of both the staples 112 and 114 and lateral movement of the one or more of the support arms 130 and 136.

Figure 13:
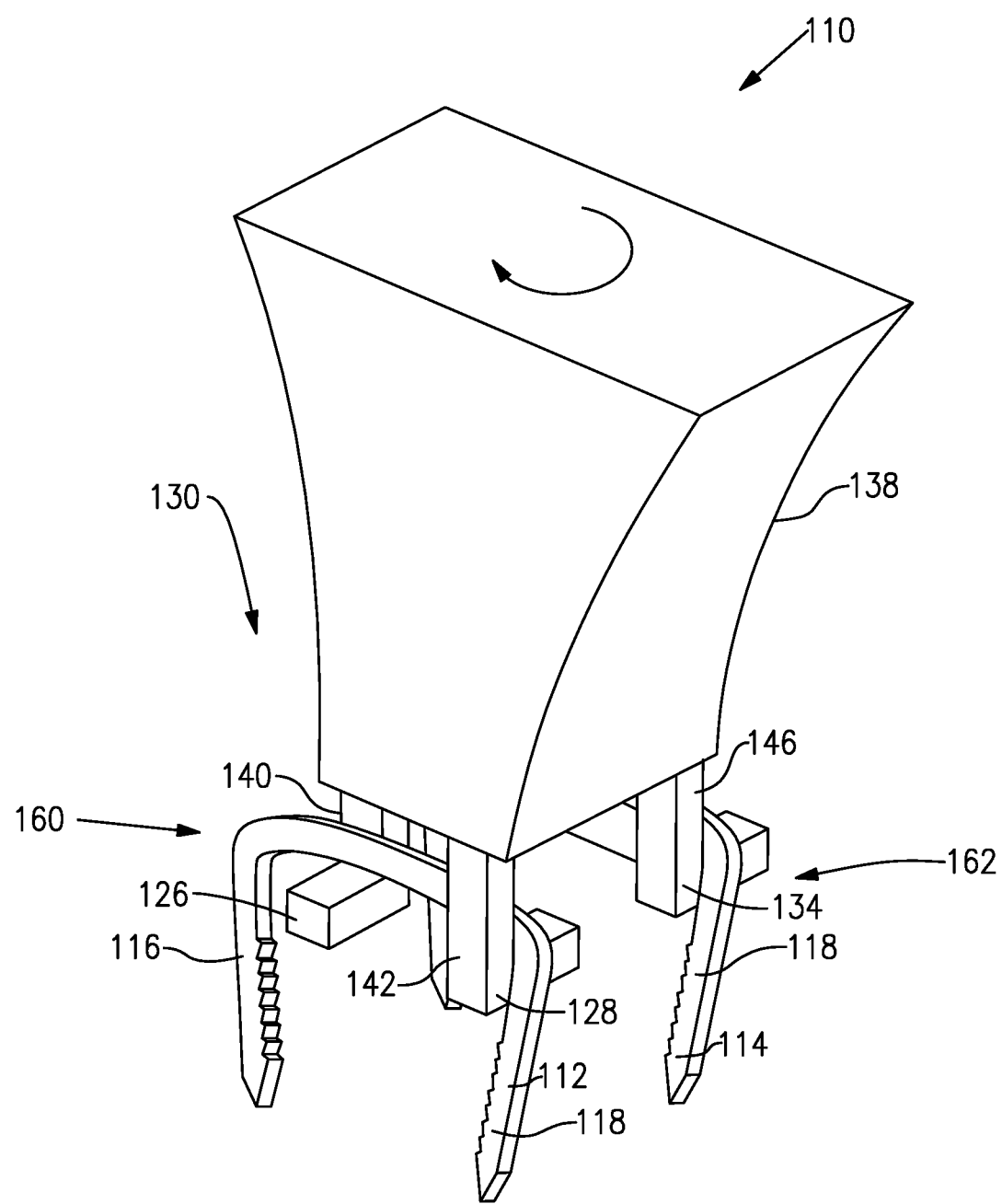
FIG. 13 illustrates a perspective view of another embodiment of the multiple staple delivery device including a first pin and a second pin of a first pin set extending from a first pin set support arm in different directions and a first pin and a second pin of a second pin set extending from a second pin set support arm in different directions.

In another example, as shown in FIG. 13, the pins 126 and 128 of the first pin set 160 extend from the first support arm 130 in misaligned directions. Similarly, pins 132 and 134 of the second pin set 162 extend from the second support arm 136 in misaligned directions. The pins 126 and 128 of the first pin set 160 can extend from the one or more first support arms 130 in opposite directions, or the pins 126 and 128 of the second pin set 162 can extend from the one or more second support arms 136 in opposite directions, or both.

In one example, one or more of the pins 126 and 128 of the first pin set 160 can extend from the first support arm 130 in a manner to support one or more first staples 112. In one example, the pins 126 and 128, or both, of the first pin set 160 can extend laterally from the first support arm 130 to support one or more first staples 112. In one example, the pins 126 and 128, or both, of the first pin set 160 can extend generally orthogonally from the first support arm 130 to support one or more first staples 112.

In one example, one or more of the pins 132 and 134 of the second pin set 162 can extend from the second support arm 136 in a manner to support one or more second staples 114. In one example, the pins 132 and 134, or both, of the second pin set 162 can extend laterally from the second support arm 136 to support one or more second staples 114. In one example, the pins 132 and 134, or both, of the second pin set 162 can extend generally orthogonally from the second support arm 136 to support one or more second staples 114.

The pins 126 and 128 of the first pin set 160 can be configured to be one or more members configured to releasably restrain one or more staples, such as first staple 112. The pins 126 and 128 of the first pin set 160 can be formed from a single pin or a plurality of pins. Similarly, the pins 132 and 134 of the second pin set 162 can be configured to be one or more members configured to releasably restrain one or more staples, such as second staple 114. The pins 132 and 134 of the second pin set 162 can be formed from a single pin or a plurality of pins.

One or more of the pins 126 and 128 of the first pin set 160 and the pins 132 and 134 of the second pin set 162 can have any appropriate configuration and is not limited to any particular shape. One or more of the pins 126 and 128 of the first pin set 160 and one or more of the pins 132 and 134 of the second pin set 162 can have cross-sectional shapes such as, but not limited to, circular, elliptical, oval, square, rectangular, symmetrical, and nonsymmetrical. In one example, the pins 126 and 128 of the first pin set 160 and the pins 132 and 134 of the second pin set 162 can be configured to have widths wider than heights of the pins 126, 128, 132, and 134, but not so wide as to prevent release of the staples 112 and 114 when the multiple staple delivery device 110 is rotated to release the staples 112 and 114.

The first support arm 130 can extend from the body 138 and support one or more pin sets, such as, but not limited to, the first pin set 160. The first support arm 130 can be rigid or flexible and can be formed from any appropriate material. The first support arm 130 can have any appropriate configuration, length, and cross-sectional shape. In one example, the first support arm 130 can extend from one proximal end 156 attached to the body 138 to a distal end 148 of the first support arm 130 to which the first pin set 160 is attached.

The second support arm 136 can extend from the body 138 and support one or more pin sets, such as, but not limited to, the second pin set 162. The second support arm 136 can be rigid or flexible and can be formed from any appropriate material. The second support arm 136 can have any appropriate configuration, length, and cross-sectional shape. In one example, the second support arm 136 can extend from one proximal end 158 attached to the body 138 to a distal end 150 of the second support arm 136 to which the second pin set 162 is attached.

In one example, the multiple staple delivery device 110 includes the body 138 that can be configured to support the support arms 130 and 136 and the pin sets 160 and 162 to enable a surgeon or other user to grasp the body 138 to position the staples 112 and 114 and perform a release maneuver to release the staples 112 and 114. The body 138 can be formed from materials such as, but not limited to, plastic, such as, but not limited to, polycarbonate or ABS. The body 138 can be formed from metal, such as, but not limited to, aluminum or stainless steel. In one example, the body 138 can be formed in a general rectangular cuboid, one or more of various ergonomic configurations, and other appropriate shapes.

During use, the first staple 112 can be loaded on the first pin set 160, and the second staple 114 can be loaded on the second pin set 162. The multiple staple delivery device 110 can be positioned as desired. The staples 112 and 114 can be released through a release maneuver. In one example, the staples 112 and 114 can be released simultaneously. The lateral release maneuver can be used to release the staples 112 and 114. The example shown in FIGS. 11 and 12 first requires removal of the retention member 154. As shown in FIG. 13, a rotational release maneuver can be used to release the staples 112 and 114.

Figure 15:
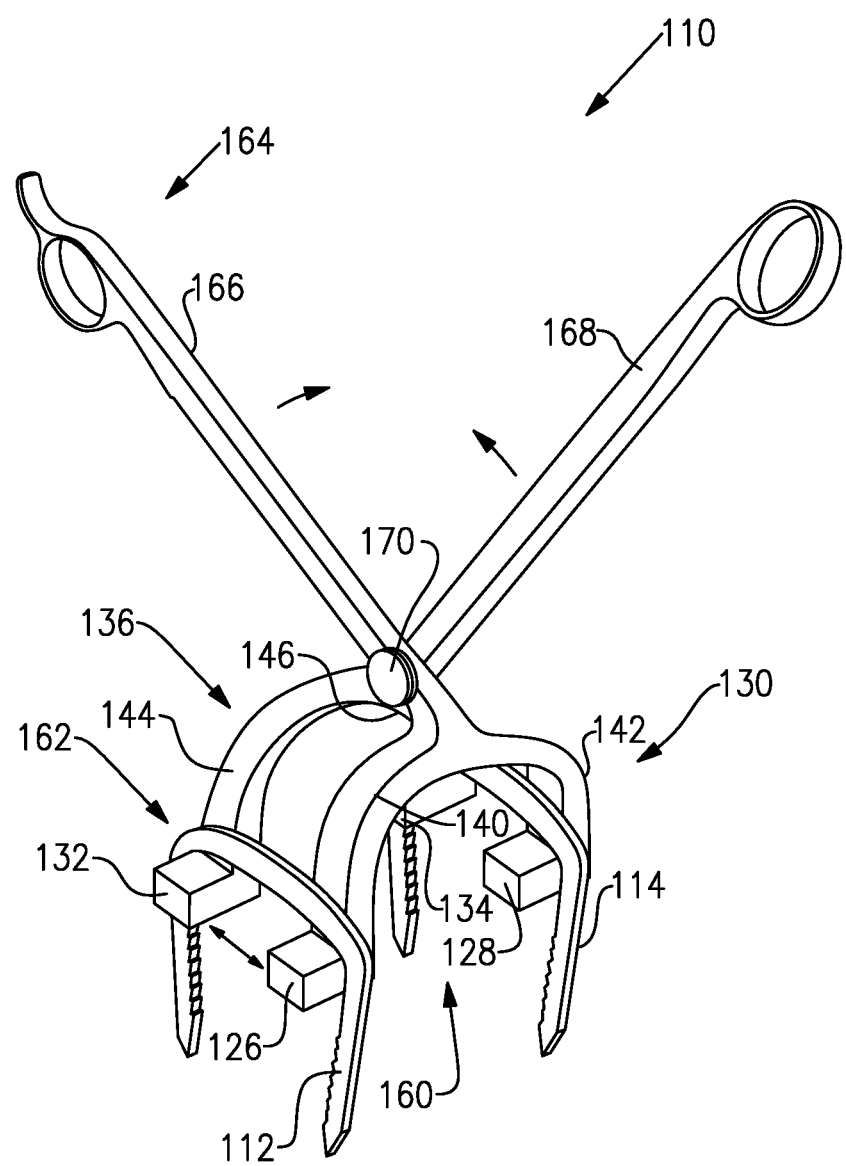
FIG. 15 illustrates a perspective view of another embodiment of the multiple staple delivery device including handles usable to control release of the first staple and the second staple, and the pins of the first pin set and the pins of the second pin set are aligned with each other.
Figure 16:
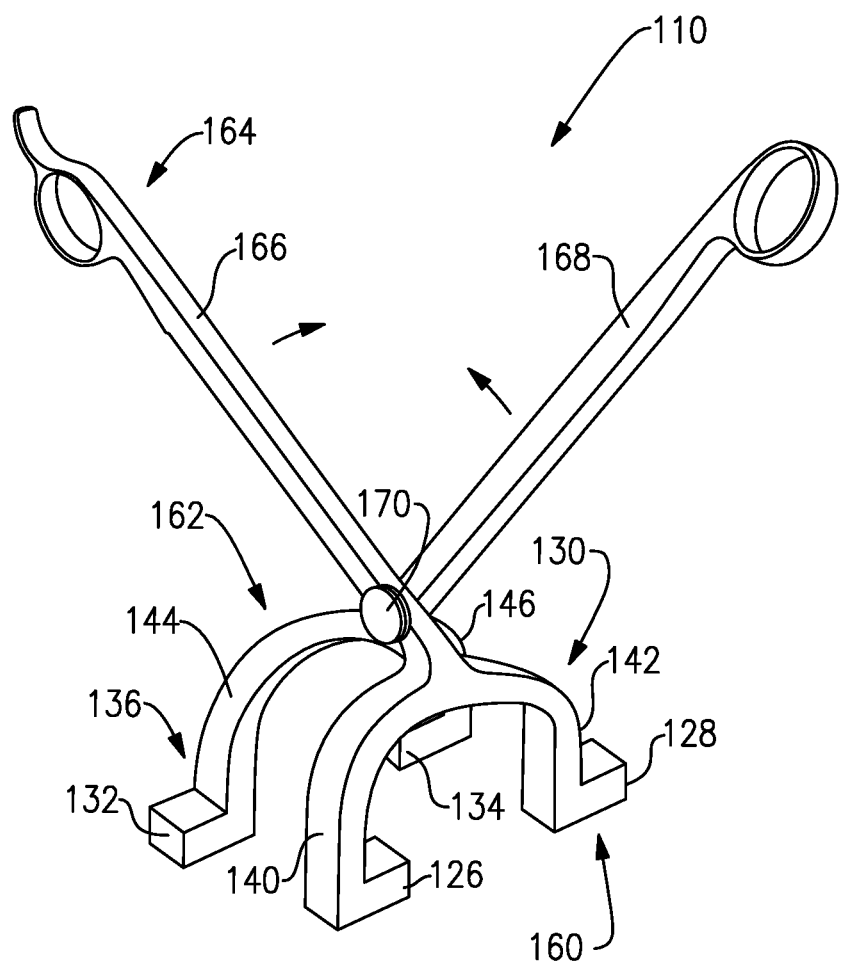
FIG. 16 illustrates a perspective view of another embodiment of the multiple staple delivery device with handles usable to control release of the first staple and the second staple, and the first pin of the first pin set extends in different direction than the first pin of the second pin set extends, and the second pin of the first pin set extends in different direction than the second pin of the second pin set extends.

In one example, as shown in FIGS. 15 to 16, the multiple staple delivery device 110 can be configured to restrain and release multiple staples 112 and 114 via a plurality of handles 164. In particular, the multiple staple delivery device 110 can include pin sets 160 and 162, as set forth herein and can include one or more first handles 166 extending from the first support arm 130. The multiple staple delivery device 110 can also include one or more second handles 168 extending from the second support arm 136. The second handle 168 is pivotally attached to the first handle 166. The handles 166 and 168 can be configured to be operable with a single hand of a surgeon. The handles 166 and 168 can have any appropriate configuration and in one example, can be ergonomically configured. The handle 166 can extend from a pivot point 170 in a generally opposite direction than a direction that the first support arm 130 extends from the pivot point 170. Similarly, the handle 168 can extend from the pivot point 170 in a generally opposite direction than a direction that the first support arm 130 extends from the pivot point 170.

The multiple staple delivery device 110 can include the first pin set 160 including the first pin 126 and the second pin 128 extending from one or more first support arms 130 and a second pin set 162 including the first pin 126 and the second pin 128 extending from one or more second support arms 136. The first pin 126 of the first pin set 160 and the first pin 132 of the second pin set 162 can be configured to support one or more first staples 112. The second pin 134 of the first pin set 160 and the second pin 134 of the second pin set 162 can be configured to support one or more second staples 114. The one or more first staples 112 and the one or more second staples 114 can be released via a release maneuver.

As shown in FIG. 15, the first pin 126 and the second pin 128 of the first pin set 160 and the first pin 132 and the second pin 134 of the second pin set 162 extend from the first support arm 130 and the second support arm 136, respectively, in the same direction. The first pin 126 and the second pin 128 of the first pin set 160 and the first pin 132 and the second pin 134 of the second pin set 162 can be aligned with each other. In this example, the release maneuver used to release the one or more first staples 112 and the one or more second staples 114 can be a lateral movement.

As shown in FIG. 16, the first pin 126 of the first pin set 160 can extend in different direction than the first pin 132 of the second pin set 162 extends. In particular, the first pin 126 of the first pin set 160 can extend in an opposite direction than the first pin 132 of the second pin set 162. The second pin 128 of the first pin set 160 can extend in an opposite direction than the second pin 134 of the second pin set 162 extends. In such a configuration, the first pin 126 of the first pin set 160 and the first pin 132 of the second pin set 162 can be aligned. Similarly, the first pin 132 of the second pin set 162 and the second pin 134 of the second pin set 162 can be aligned. In such example, the release maneuver used to release the one or more first staples 112 and the one or more second staples 114 can be a rotational movement.

During use, the first staple 112 can be loaded on the first pin set 160, and the second staple 114 can be loaded on the second pin set 162. The multiple staple delivery device 110 can be positioned as desired. The staples 112 and 114 can be released through a release maneuver involving releasing at least one handle 164 to allow the handles 164 to separate from each other, thereby relieving pressure placed on the staples 112 and 114 from the pin sets 160 and 162. For the multiple staple delivery device shown in FIG. 14, the staples 112 and 114 can be released with a lateral movement. For the multiple staple delivery device shown in FIG. 15, the staples 112 and 114 can be released with a rotational movement.

Figure 17:
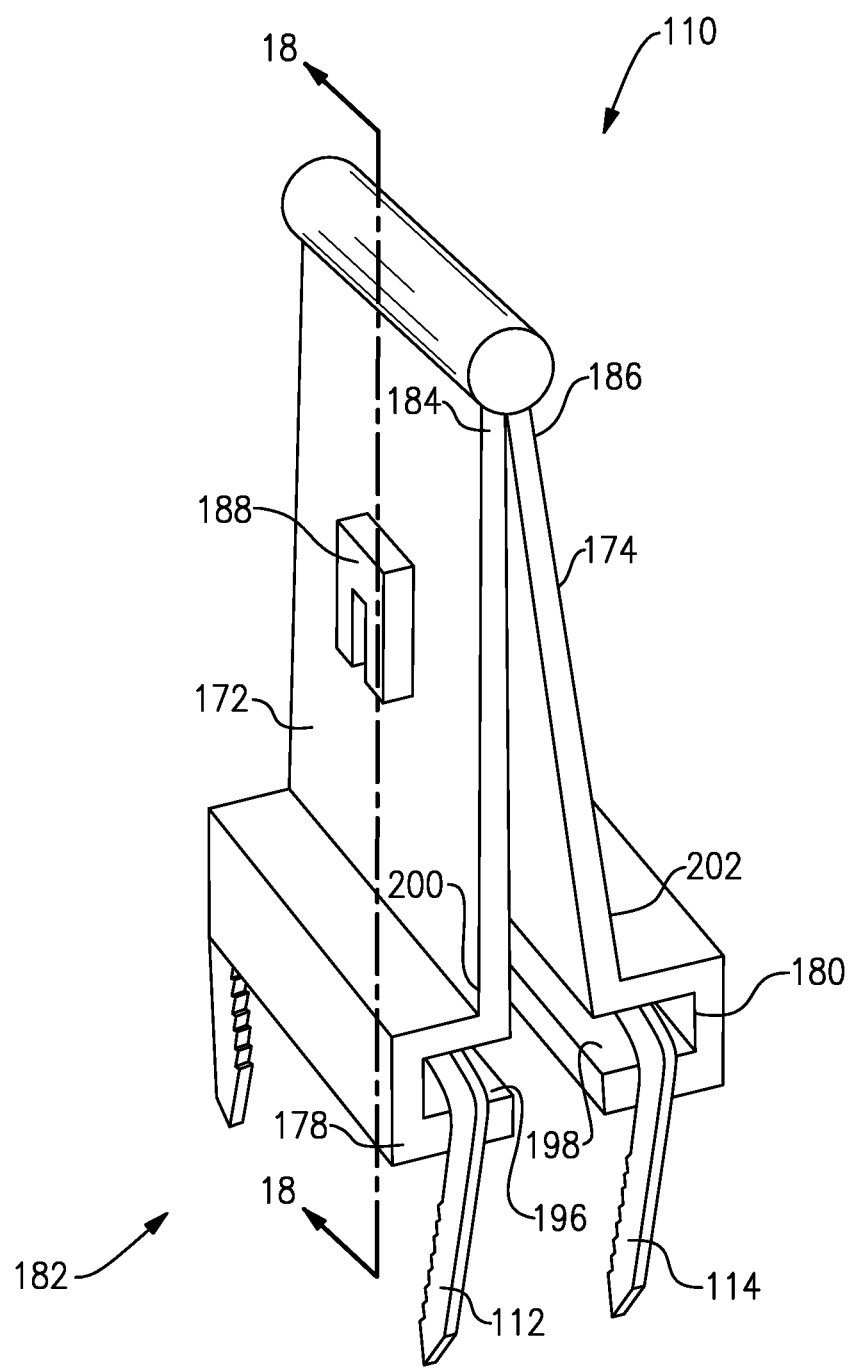
FIG. 17 illustrates a perspective view of another embodiment of the multiple staple delivery device including a first body and a second body pivotally coupled together, each with a receiver configured to receive a staple.
Figure 18:
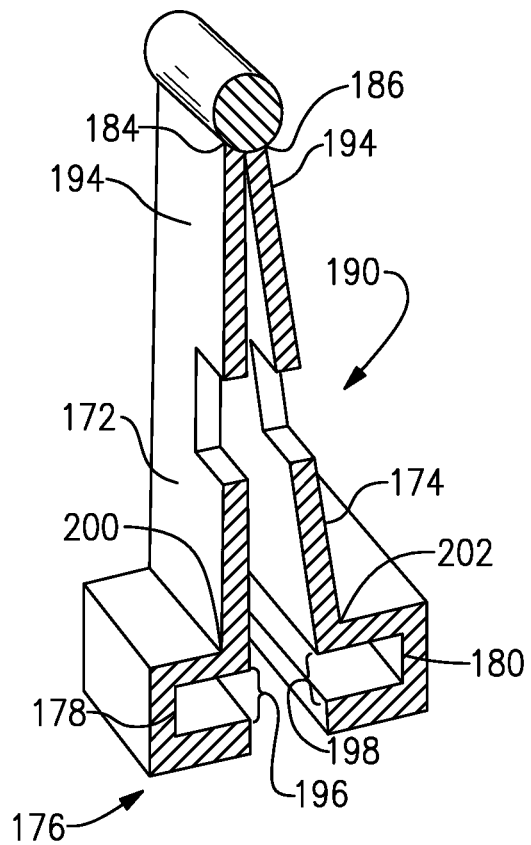
FIG. 18 illustrates a cross-sectional view of the multiple staple delivery device of FIG. 17 taken along section line 18-18.
Figure 19:
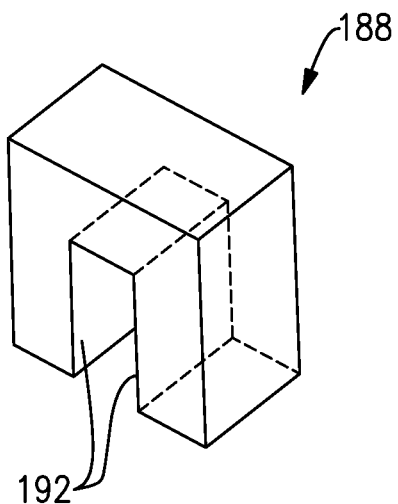
FIG. 19 illustrates a perspective view of a restraint member configured to restrain the bodies in a closed position.

As shown in FIGS. 17 and 18, the multiple staple delivery device 110 can include a first body 172 pivotally coupled to a second body 174. The first body 172 and the second body 174 can be configured to pivot between a closed position 176 (as shown in FIG. 18) in which one or more first staples 112 is contained in a first receiver 178 and one or more second staples 114 is contained in the second receiver 180 and an open position 182 in which one or more first staples 112 is released from the first receiver 178 and one or more second staples 114 is released from the second receiver 180. In one example, the first body 172 can be pivotally coupled to the second body 174 at distal ends 184 and 186 of the bodies 172 and 174, respectively. In one example, the first body 172 can be a plate, such as, but not limited to, a flat plate. The second body 174 can be a plate, such as, but not limited, to a flat plate. The bodies 172 and 174 can have any appropriate configuration and can be ergonomically designed. The bodies 172 and 174 can be biased away from each other. The biasing force can be created via many different designs, for example, and not by way of limitation, a spring loaded hinge. The bodies 172 and 174 are integrally formed and folded into a shape, where the bodies 172 and 174 contact each other and the like.

The multiple staple delivery device 110 can also include a restraint member 188 configured to restrain the bodies 172 and 174 in the closed position 176. The restraint member 188 can be configured to be positioned within a restraint receiver 190 in the bodies 172 and 174. In one example, the restraint receiver 190 in each of the bodies 172 and 174 can be a hole. The restraint member 188 can be, but is not limited to being, a C shaped restraint member 188 configured to be moved between the closed position 176 and the open position 182. In the restrained position, the C shaped restraint member 188 can place inner side surfaces 192 of the C shaped restraint member 188 in contact with outer surfaces 194 of the bodies 172 and 174. The C shaped restraint member 188 can be moved into the open position 182 by sliding the C shaped restraint member 188 relative to the bodies 172 and 174 so that the inner side surfaces 192 of the C shaped restraint member 188 are removed from contact with the outer surfaces 194 of the bodies 172 and 174, allowing the bodies 172 and 174 to move apart.

The multiple staple delivery device 110 can include the first receiver 178 coupled to the first body 172 and configured to receive one or more first staples 112 and the second receiver 180 coupled to the second body 174 and configured to receive one or more second staples 114. The receivers 178 and 180 can each have staple receiving openings 196 and 198, respectively, that face each other such that one or more first staples 112 and one or more second staples 114 are prevented from being released in the closed position 176 (as shown in FIG. 18) and permitted to be released through the staple receiving openings 196 and 198 of the receivers 178 and 180, respectively, when in the open position 182 (as shown in FIG. 17).

The first receiver 178 can be configured as a C channel with the opening 196 facing the second receiver 180. The C channel forming the first receiver 178 can extend for part of or all of a width of the first body 172. The first receiver 178 can be positioned at a distal end 200 of the first body 172 that is on an opposite end of the first body 172 from the end 184 where the first body 172 is pivotally coupled to the second body 174.

The second receiver 180 can be configured as a C channel with an opening 198 facing the second receiver 180. The C channel forming the second receiver 180 can extend for part of or all of a width of the second body 174. The second receiver 180 can be positioned at a distal end 202 of the second body 174 that is on an opposite end of the second body 174 from the end 186 where the second body 174 is pivotally coupled to the first body 172. The receivers 178 and 180 can have identical configurations or can be different.

During use, a first staple 112 can be loaded into a first receiver 178, and a second staple 114 can be loaded into a second receiver 180. The multiple staple delivery device 110 can be positioned as desired. The staples 112 and 114 can be released through a release maneuver in which the restraint member 188 can be moved to release the bodies 172 and 174. Such action releases the staples 112 and 114 through the staple receiving openings 196 and 198, respectively.

Figure 20:
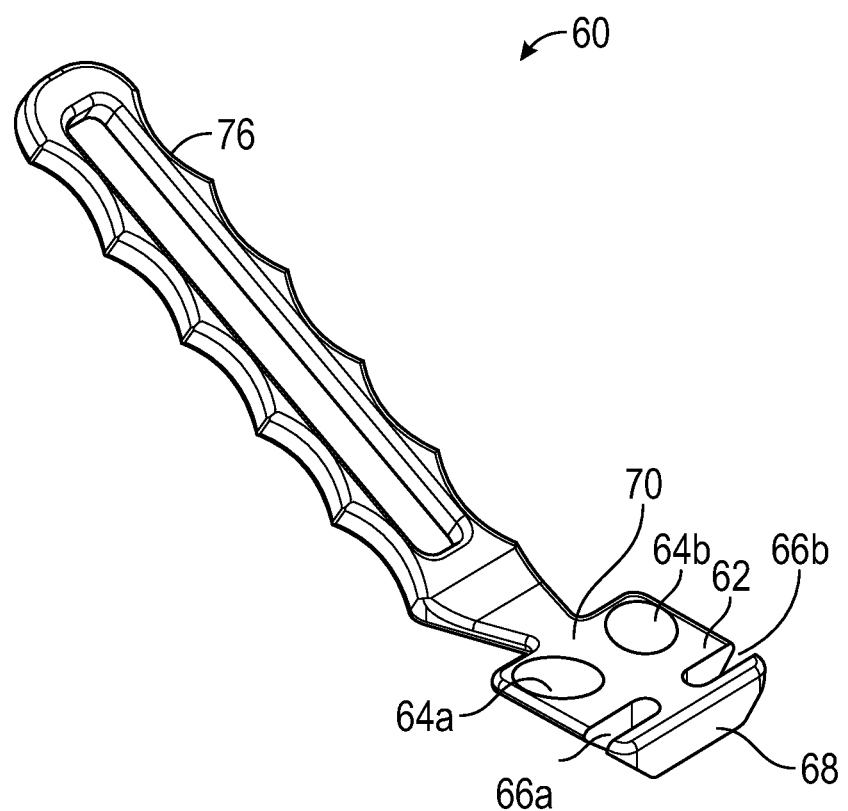
FIG. 20 illustrates a perspective view of an interfragmentary drill guide.
Figure 21:
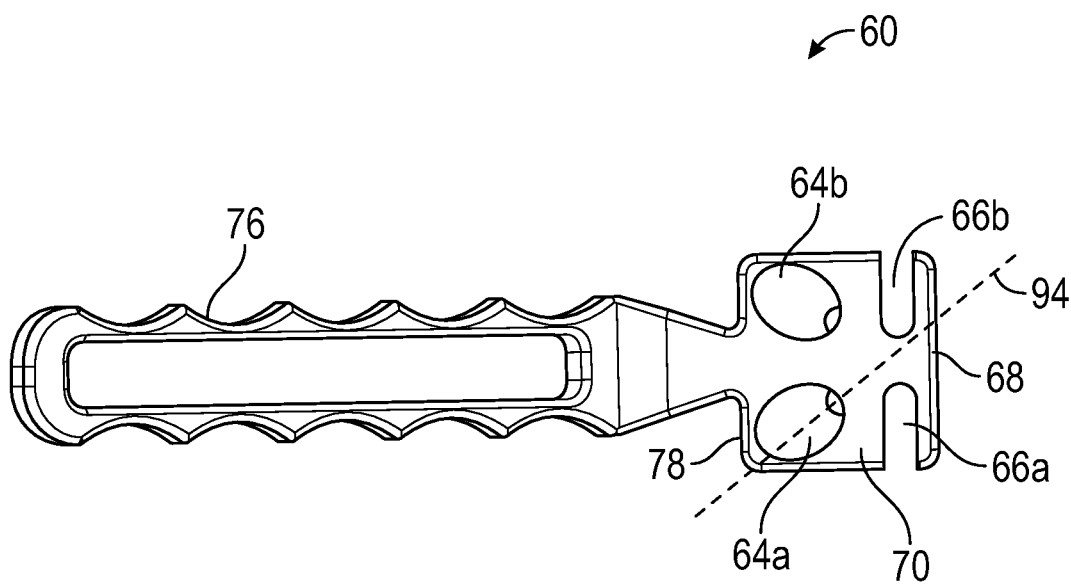
FIG. 21 illustrates a top view of the interfragmentary drill guide.
Figure 22:
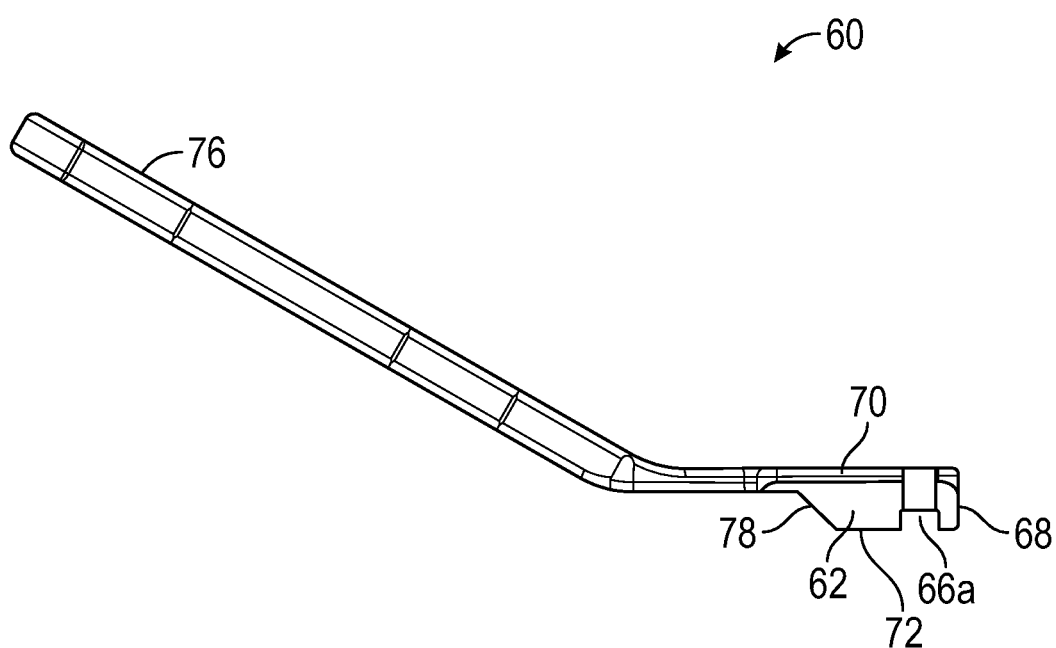
FIG. 22 illustrates a side view of the interfragmentary drill guide.

FIGS. 20 to 22 illustrate a first example interfragmentary drill guide 60 used to drill a screw passage that spans a fracture line 100 in a fractured bone 98. The screw passage receives an interfragmentary screw 102 to supplement a staple that is used to repair a fracture, such as the staple 12 described above. The staple 12 will be described below using the terminology used above and as shown in FIGS. 6 and 7. The interfragmentary drill guide 60 directs a drill or a guide wire across the fracture line 100 without interfering with the legs 16 and 18 of the staple 12 that is already installed in the fractured bone 98 or a staple 12 that will be installed in the fractured bone 98 after drilling.

The interfragmentary drill guide 60 includes a body 62 including at least one hole 64. The hole 64 receives the drill to form a screw passage in the fractured bone 98. The hole 64 is shaped to guide the drill so that the screw passage will have a specific trajectory 94 within the fractured bone 98. The screw passage receives an interfragmentary screw 102 that provides additional fixation across the fracture line 100 in addition to the staple 12. In an example, there are two holes 64a and 64b each used to form one screw passage. The holes 64a and 64b each define the trajectory 94 so that the drilled screw passages and the interfragmentary screws 102 do not intersect with the legs 16 and 18 of the staple 12 once installed across the fracture line 100 of the fractured bone 98. One or two screw passages can be formed in the fractured bone 98.

Figure 26:
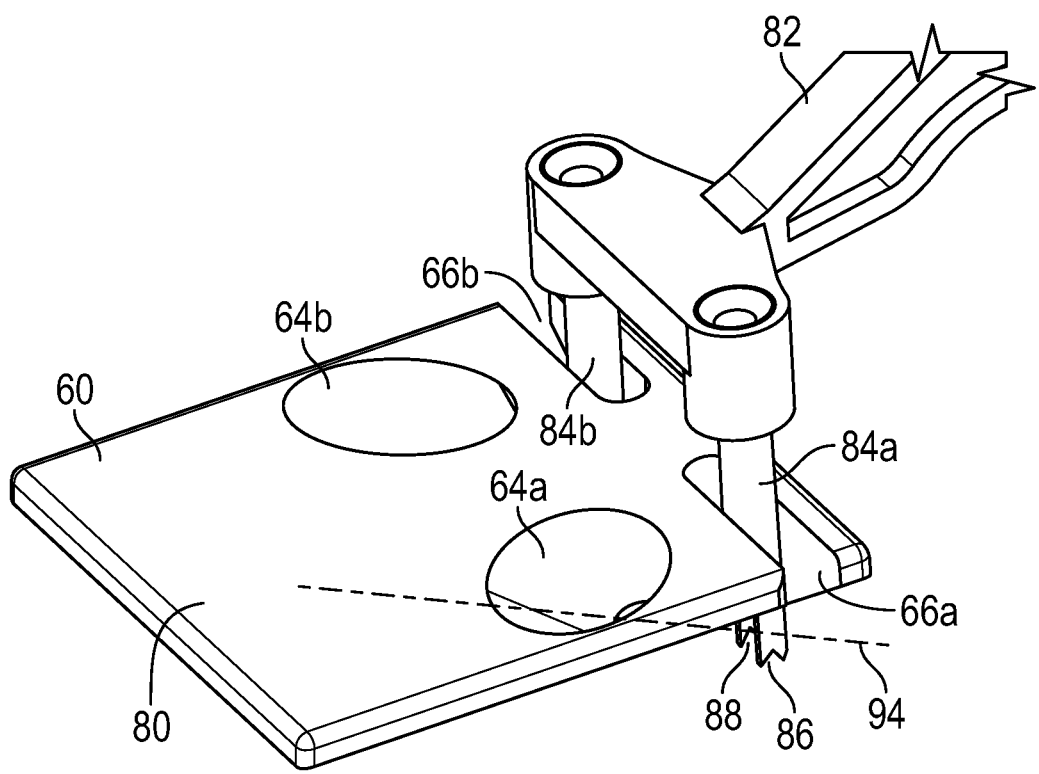
FIG. 26 illustrates a perspective view of the another interfragmentary drill guide before staple implantation.

The interfragmentary drill guide 60 also includes two slots 66a and 66b proximate to a face 68 of the body 62 that each receive a portion of a drill guide 82 (shown in FIG. 26). An upper surface 70 and a bottom surface 72 of the body 62 are substantially flat. The face 68 of the body 62 is substantially perpendicular to the upper surface 70 of the body 62. In an example, the upper surface 70 is substantial square shaped. The interfragmentary drill guide 60 also includes an elongated recess 74 (shown in FIGS. 27A and 27B) that can receive the bridge 14 of a staple 12 installed across the fracture line 100 for proper alignment.

Figure 23:
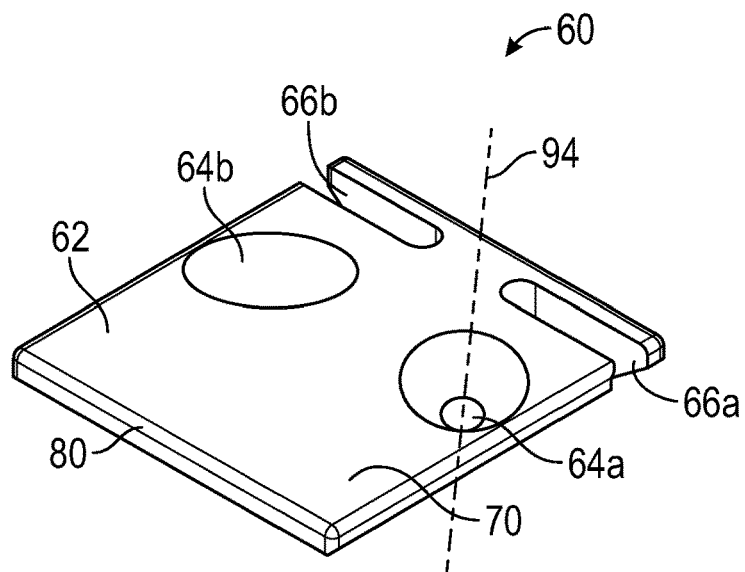
FIG. 23 illustrates a perspective view of another interfragmentary drill guide.
Figure 24:
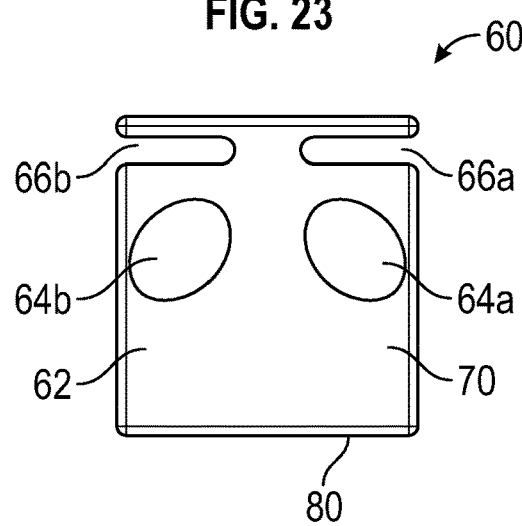
FIG. 24 illustrates a top view of the another interfragmentary drill guide.
Figure 25:
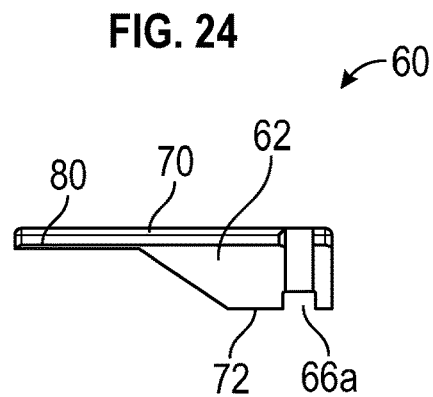
FIG. 25 illustrates a side view of the another example interfragmentary drill guide.

In an example, the interfragmentary drill guide 60 includes an elongated handle 76 attached to a side 78 of the body 62 opposite to the face 68. In an example, the elongated handle 76 extends approximately 45° relative to the upper surface 70 of the body 62. In an example, the body 62 and the handle 76 define a single integral monolith component. In another example shown in FIGS. 23 to 25, a handle 80 extends substantially parallel to the body 62 and is continuous with the upper surface 70 of the body 62.

In an example, the interfragmentary drill guide 60 is used to drill the screw passages prior to implantation of the staple 12 across the fracture line 100 of the fractured bone 98. The bottom surface 72 of the interfragmentary drill guide 60 is placed on top of the fractured bone 98. A drill guide 82 (shown in FIG. 26) includes two drill tubes 84a and 84b, and each of the two tubes 84a and 84b is located in one of the two slots 66a and 66b, respectively, of the interfragmentary drill guide 60. Each of the drill tubes 84a are located on the opposite side of the fracture line 100 than the other drill tube 84b. The two drill tubes 84a and 84b guide a drill to form drill passages that will receive the legs 16 and 18 of the staple 12.

A bottom surface of each of the drill tubes 84a and 84b includes a plurality of teeth 86 that engage the fractured bone 98 and prevent slippage of the drill guide 82 relative to the fractured bone 98. A bottom portion of each of the drill tubes 84a and 84b also includes a slot 88 that assists with installation of the staple 12. If the screw passages formed by the drill are directed towards the drill tubes 84a and 84b, the trajectory 94 will not intersect the drill tubes 84a and 84b and passes through the slot 88 in the drill tubes 84a and 84b.

Figure 27A:
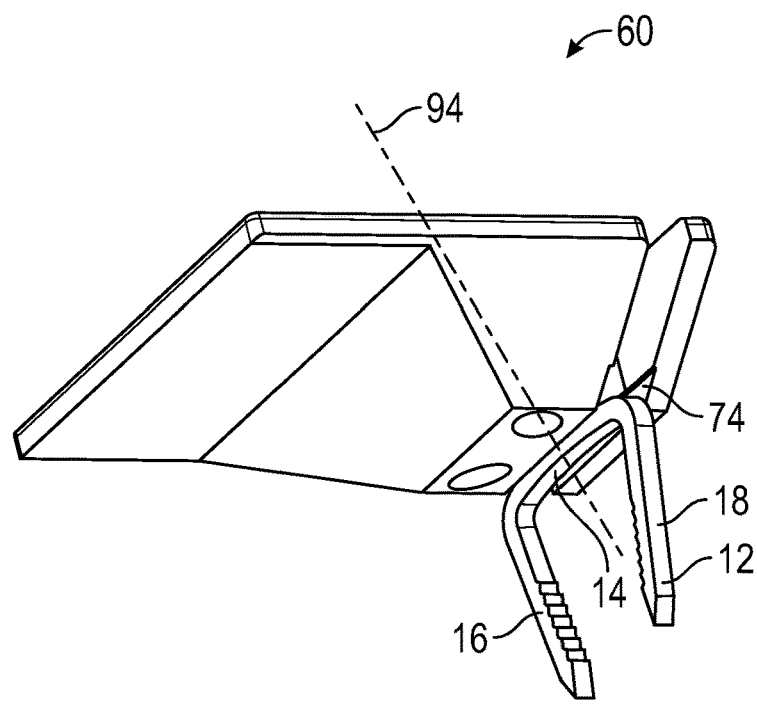
FIG. 27A illustrates a perspective view of the another interfragmentary drill guide before staple implantation.
Figure 27B:
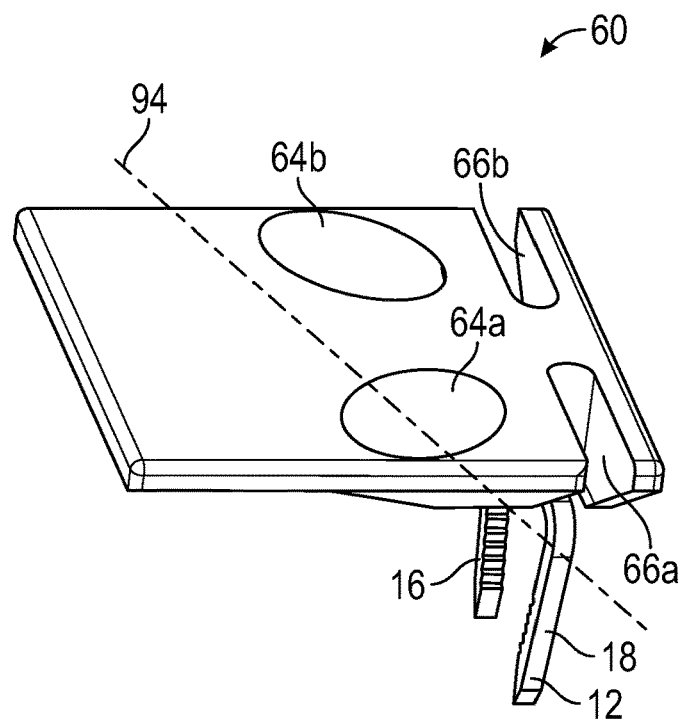
FIG. 27B illustrates a perspective view of the another interfragmentary drill guide before staple implantation.

FIGS. 27A and 27B illustrate the interfragmentary drill guide 60 employed with a staple 12 already installed across the fracture line 100 of the fractured bone 98. The interfragmentary drill guide 60 is positioned such that the bridge 14 of the staple 12 is received in the elongated recess 74 of the body 62, preventing movement of the interfragmentary drill guide 60 relative to the staple 12. At least one of the drilling holes 64a and 64b is used to guide the drill to form at least one screw passage with a defined trajectory 94 that does not intersect the legs 16 and 18 of the staple 12. In an example, the recess 74 is machined in the interfragmentary drill guide 60. In another example, the recess 74 is located between the face 68 of the body 62 and the two drilling holes 64a and 64b.

Figure 28:
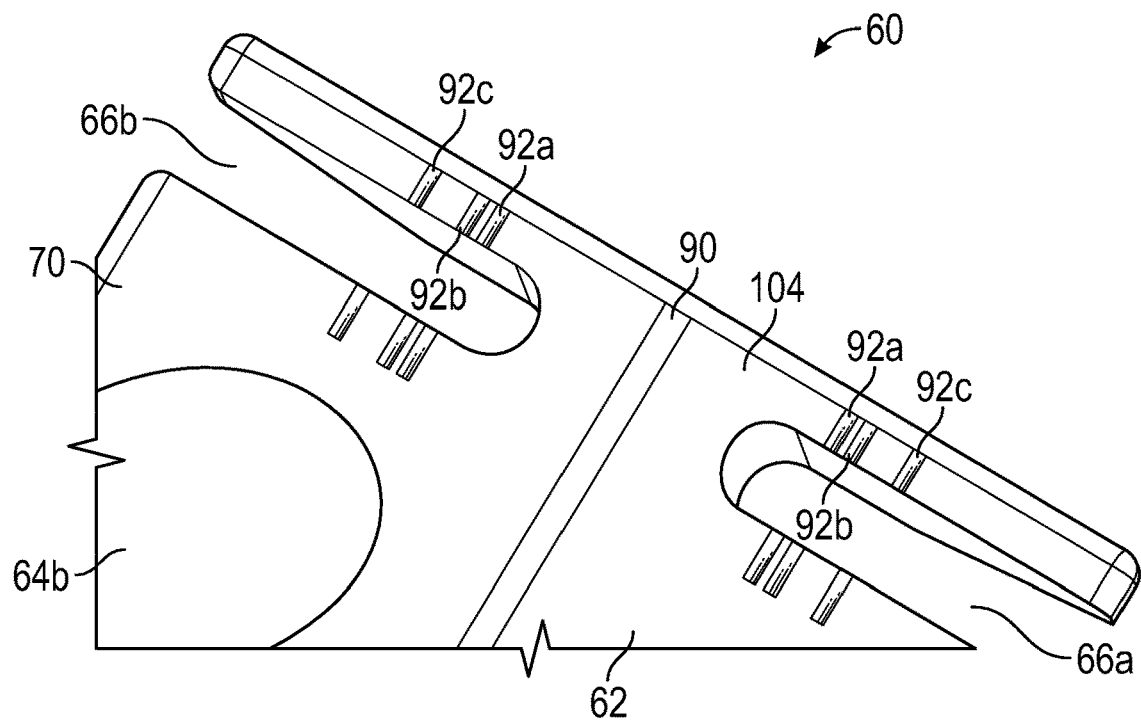
FIG. 28 illustrates markings on the interfragmentary drill guide.

FIG. 28 illustrates laser markings on an upper surface 104 of the interfragmentary drill guide 60 that provide a visual indication that the interfragmentary drill guide 60 is aligned with the staple 12 prior to drilling. A central marking 90 extends from the face 68 and between the two slots 66a and 66b, and the central marking 90 is aligned with the fracture line 100 during use.

The interfragmentary drill guide 60 also includes a plurality of paired staple markings 92a, 92b, 92c that are substantially parallel to the central marking 90. Each pair of staple markings 92a, 92b, 92c includes one staple marking associated with one slot 66a and a corresponding staple marking 92a, 92b, 92c associated with the other slot 66b. The two paired staple markings 92a, 92b, 92c are each equidistant from the central marking 90. When the interfragmentary drill guide 60 is positioned over the staple 12, each end of the bridge 14 of the staple 12 visually aligns with one of a pair of staple markings 92a, 92b, 92c, indicating that the interfragmentary drill guide 60 is aligned relative to the staple 12 so that the trajectory 94 of the screw passages do not intersect the legs 16 and 18 of the staple 12.

The interfragmentary drill guide 60 can employ the elongated recess 74 or the plurality of marked lines 92a, 92b, 92c or both. Once the holes are drilled in the fractured bone 98, the interfragmentary screw 102 can be received in each screw passage to supplement the staple 12.

Figure 29:
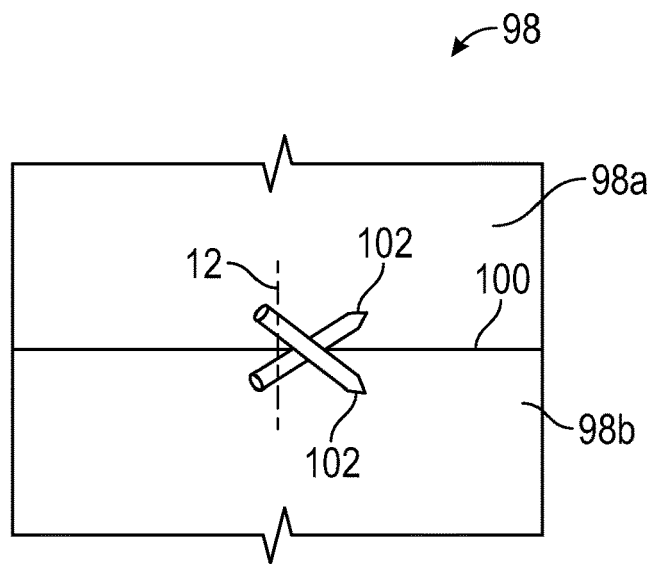
FIG. 29 illustrates a top view of a fractured bone with an interfragmentary screw and a staple.

As shown in FIG. 29, the fractured bone 98 includes the first bone fragment 98a and the second bone fragment 98b separated by the fracture line 100, and the staple 12 or staples 12a and 12b span across the fracture line 100. In the example illustrated, two interfragmentary screws 102 span the fracture line 100 of the fractured bone 98 to assist with compression. Only one interfragmentary screw 102 can also be employed.

A method of compressing a fracture includes aligning the body 62 of the interfragmentary drill guide 60 relative to the fractured bone 98 such that each of the two slots 66a and 66b and each of the two holes 64a and 64b of the body 62 of the interfragmentary drill guide 60 are located on opposing sides of the fracture line 100 of the fractured bone 98. The method also includes positioning each of the tubes 84a and 84b of the drill guide 82 in one of the two slots 66a and 66b of the interfragmentary drill guide 60 to guide a drill to form a drill passage located on opposing sides of the fracture line 100 of the fractured bone 98. The drill passages each receive one of the legs 16 and 18 of the staple 12. The method also includes forming a screw passage through at least one of the holes 64a and 64b of the body 62 of the interfragmentary drill guide 60, and the screw passage has a trajectory that crosses the fracture line 100 of the fractured bone 98 that does not intersect the legs 16 and 18 of the staple 12.

The step of aligning the body 62 of the interfragmentary drill guide 60 can include receiving the bridge 14 of the staple 12 in the elongated recess 74 on the bottom surface 72 of the interfragmentary drill guide 60. The step of aligning the body 62 of the interfragmentary drill guide 60 can also include aligning a pair of staple markings 92a, 92b, 92c on an upper surface 104 of the body 62 of the interfragmentary drill guide 60 with ends of the bridge 14 of the staple 12 to provide a visual indication of alignment of the interfragmentary drill guide 60 with the staple 12.

The foregoing description is only exemplary of the principles of the invention. Many modifications and variations are possible in light of the above teachings.

What is claimed is:

1. An insertion system comprising:
   a body including a first side and an opposing second side, wherein a first staple includes a first bridge and a first pair of legs each attached to the first bridge at a first elastic hinge region and a second staple including a second bridge and a second pair of legs each attached to the second bridge at a second elastic hinge region, wherein the first staple and the second staple are mounted to the body, and the first staple and the second staple are identical and comprise Nitinol;
   a first pair of plates each mounted to the first side of the body by a first proximal pin and a second pair of plates each mounted to the second side of the body by a second proximal pin, wherein each of the first pair of plates includes a first distal pin and each of the second pair of plates includes a second distal pin, and the first staple is mounted on the first distal pins and the second staple is mounted on the second distal pins, each of the first distal pins of the first pair of plates are located under one of the first elastic hinge regions of the first staple, and each of the second distal pins of the second pair of plates are located under one of the second elastic hinge regions of the second staple;
   a handle moveable in a first direction and an opposing second direction;
   a plunger having a proximal end and a distal end, wherein movement of the handle causes the distal end of the plunger to push against a bending structure; and
   the bending structure capable of engaging the first bridge and the second bridge, wherein rotation of the handle in the first direction causes the bending structure to engage and bend the first bridge and the second bridge simultaneously to configure the first staple and the second staple from an unrestrained state in which the first pair of legs and the second pair of legs are angled inwardly to a strained state in which the first pair of legs and the second pair of legs are substantially perpendicular to the bridge, and rotation of the handle in the opposing second direction causes the threaded rod and the plunger to move proximally and the bending structure removes pressure from the first bridge and the second bridge.

2. An insertion system comprising:
   a body, wherein a first staple includes a first bridge and a first pair of legs each attached to the first bridge at a first elastic hinge region and a second staple that includes a second bridge and a second pair of legs each attached to the second bridge at a second elastic hinge region, and the first staple and the second staple are mounted to the body;
   a bending structure capable of bending the first bridge and the second bridge, wherein the bending structure bends the first bridge and the second bridge to configure the first staple and the second staple from an unrestrained state in which the first pair of legs and the second pair of legs are angled inwardly to a strained state in which the first pair of legs and the second pair of legs are substantially perpendicular to the bridge.

3. The insertion system as recited in claim 2 wherein the first staple and the second staple are identical.

4. The insertion system as recited in claim 2 wherein the first staple and the second staple have different sizes.

5. The insertion system as recited in claim 2 wherein the first staple and the second staple comprise Nitinol.

6. The insertion system as recited in claim 2 wherein the body includes a first side and an opposing second side, wherein a first pair of plates are each mounted to the first side of the body by a first proximal pin and a second pair of plates are each mounted to the second side of the body by a second proximal pin, each of the first pair of plates includes a first distal pin and each of the second pair of plates includes a second distal pin, and the first staple is mounted on the first distal pins and the second staple is mounted on the second distal pins.

7. The insertion system as recited in claim 6 wherein each of the first distal pins of the first pair of plates are located under one of the first elastic hinge regions of the first staple, and each of the second distal pins of the second pair of plates are located under one of the second elastic hinge regions of the second staple.

8. The insertion system as recited in claim 2 including a handle moveable in a first direction and an opposing second direction, wherein the bending structure bends the first bridge and the second bridge to configure the first staple and the second staple from the unrestrained state to the strained state.

9. The insertion system as recited in claim 8 wherein the multi-staple inserter includes a threaded rod having a proximal end and a distal end and a plunger having a proximal end and a distal end, the body includes an internally threaded passage, the threaded rod is configured to mate with the internally threaded passage of the body, and the handle is mounted to the proximal end of the threaded rod.

10. The insertion system as recited in claim 9 wherein the handle rotates, rotation of the handle in the first direction causes the threaded rod to move distally such that the distal end of the threaded rod pushes against the proximal end of the plunger to translate the plunger distally, the distal end of the plunger applies pressure on the bending structure to bend the bending structure, and the bending structure simultaneously engages and bends the first bridge and the second bridge to bias the first legs and the second legs of the first staple and the second staple outwardly to configure the first staple and the second staple from the unrestrained state to the strained state.

11. The insertion system as recited in claim 2 including a first pin set comprising a first pin and a second pin extending from a first pin set support arm and configured to support the first staple, a second pin set comprising a first pin and a second pin extending from a second pin set support arm and configured to support the second staple, wherein the body supports the first pin set support arm and the second pin set support arm, and the first staple and the second staple are released via a release maneuver, and the first pin and the second pin of the first pin set and the first pin and the second pin of the second pin set extend from the first pin set support arm and the second pin set support arm, respectively, in the same direction.

12. The insertion system as recited in claim 11 wherein the release maneuver comprises lateral movement of the first pin set support arm and the second pin set support arm.

13. The insertion system as recited in claim 11 including a retention member removably positioned between the first pin and the second pin of the first pin set and between the first pin and the second pin of the second pin set.

14. The insertion system as recited in claim 13 wherein the release maneuver comprises movement of the retention member sufficient to permit release of both the first staple and the second staple and lateral movement of the first pin set support arm and the second pin set support arm.

15. The insertion system as recited in claim 2 including a first pin set comprising a first pin and a second pin extending from a first pin set support arm and configured to support the first staple, a second pin set comprising a first pin and a second pin extending from a second pin set support arm and configured to support the second staple, wherein the body supports the first pin set support arm and the second pin set support arm, the first pin and the second pin of the first pin set extend from the first pin set support arm in misaligned directions, and the first pin and the second pin of the second pin set extend from the second pin set support arm in misaligned directions.

16. The insertion system as recited in claim 2 including a first pin set comprising a first pin and a second pin extending from a first pin set support arm and configured to support the first staple, a second pin set comprising a first pin and a second pin extending from a second pin set support arm and configured to support the second staple, wherein the body supports the first pin set support arm and the second pin set support arm, the first pin and the second pin of the first pin set extend from the first pin set support arm in opposite directions, and the first pin and the second pin of the second pin set extend from the second pin set support arm in opposite directions.

17. The insertion system as recited in claim 2 comprising:
a first pin set comprising a first pin and a second pin extending from a first pin set support arm,
a second pin set comprising a first pin and a second pin extending from a second pin set support arm,
a first handle extending from the first pin set support arm,
a second handle extending from the second pin set support arm, wherein the second handle is pivotally attached to the first handle,
wherein the first pin set first pin and the second pin set first pin are configured to support the first staple, the first pin set second pin and the second pin set second pin are configured to support the second staple, and the first staple and the second staple are released via a release maneuver.

18. The insertion system as recited in claim 17 wherein the first pin and the second pin of the first pin set and the first pin and the second pin of the second pin set extend from the first pin set support arm and the second pin set support arm, respectively, in the same direction.

19. The insertion system as recited in claim 17 wherein the first pin of the first pin set extends in a different direction than the first pin of the second pin set, and the second pin of the first pin set extends in a different direction than the second pin of the second pin set.

20. A method of inserting at least two staples into a bone comprising:
moving a handle of a multi-staple inserter of an insertion system in a first direction to configure the at least two staples mounted to a body of the multi-staple inserter from an unrestrained state to a strained state to bend a bridge of the at least two staples to move a pair of legs of the at least two staples to be substantially perpendicular to the bridge;
inserting each of the pair of legs of the at least two staples into a set of holes in the bone; and
releasing the at least two staples from the body of the multi-staple inserter.

* * * * *